United States Patent
Fukazawa et al.

(10) Patent No.: US 10,614,555 B2
(45) Date of Patent: Apr. 7, 2020

(54) CORRECTION PROCESSING OF A SURGICAL SITE IMAGE

(71) Applicant: SONY CORPORATION, Tokyo (JP)

(72) Inventors: Kentaro Fukazawa, Tokyo (JP); Yuki Sugie, Kanagawa (JP); Takami Mizukura, Kanagawa (JP); Hiroshi Ichiki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 38 days.

(21) Appl. No.: 15/772,560

(22) PCT Filed: Dec. 28, 2016

(86) PCT No.: PCT/JP2016/089036
§ 371 (c)(1),
(2) Date: May 1, 2018

(87) PCT Pub. No.: WO2017/122541
PCT Pub. Date: Jul. 20, 2017

(65) Prior Publication Data
US 2019/0096037 A1    Mar. 28, 2019

(30) Foreign Application Priority Data
Jan. 13, 2016   (JP) ................................ 2016-004504

(51) Int. Cl.
*H04N 7/18*      (2006.01)
*G06T 5/00*      (2006.01)
(Continued)

(52) U.S. Cl.
CPC .......... *G06T 5/002* (2013.01); *A61B 1/00009* (2013.01); *A61B 1/00048* (2013.01);
(Continued)

(58) Field of Classification Search
CPC ...................................................... G06T 5/002
(Continued)

(56) References Cited

U.S. PATENT DOCUMENTS 9,066,658 B2 *  6/2015  Hamel ............... A61B 1/00009
2006/0126083 A1 * 6/2006  Kurumisawa ............ G09G 3/20
358/1.2
(Continued)

FOREIGN PATENT DOCUMENTS

JP    2001-211325 A    8/2001
JP    2003-24273 A     1/2003
(Continued)

OTHER PUBLICATIONS

International Search Report dated Mar. 14, 2017 in PCT/JP2016/089036 filed Dec. 28, 2016.

*Primary Examiner* — Leron Beck
(74) *Attorney, Agent, or Firm* — Xsensus, LLP

(57) ABSTRACT

An image processing apparatus includes processing circuitry configured to perform correction processing on the surgical site image as a captured surgical site on the basis of information related to display of a display apparatus that displays the surgical site image. The image processing apparatus is included in a surgical system that displays the surgical site image photographed by an endoscope on a monitor.

18 Claims, 22 Drawing Sheets

(51) Int. Cl.
- *A61B 1/04* (2006.01)
- *A61B 90/00* (2016.01)
- *A61B 1/00* (2006.01)
- *G06T 7/70* (2017.01)
- *A61B 90/30* (2016.01)

(52) U.S. Cl.
CPC .............. *A61B 1/04* (2013.01); *A61B 90/361* (2016.02); *G06T 5/001* (2013.01); *G06T 5/003* (2013.01); *G06T 5/006* (2013.01); *G06T 5/009* (2013.01); *G06T 7/70* (2017.01); *A61B 1/00193* (2013.01); *A61B 2090/306* (2016.02); *A61B 2090/371* (2016.02); *A61B 2090/372* (2016.02); *A61B 2090/373* (2016.02); *G06T 2207/10028* (2013.01); *G06T 2207/10068* (2013.01); *G06T 2207/20182* (2013.01); *G06T 2207/20192* (2013.01)

(58) Field of Classification Search
USPC .......................................................... 348/65
See application file for complete search history.

(56) References Cited

U.S. PATENT DOCUMENTS

| | | | | |
|---|---|---|---|---|
| 2007/0156017 A1* | 7/2007 | Lamprecht | ......... | A61B 1/00193 600/102 |
| 2010/0073773 A1* | 3/2010 | Hotta | ..................... | G02B 27/01 359/630 |
| 2011/0082369 A1* | 4/2011 | Mohr | ........................ | G06T 5/50 600/431 |
| 2011/0115766 A1* | 5/2011 | Kerofsky | ................ | G06T 5/003 345/207 |
| 2011/0122232 A1* | 5/2011 | Hoshino | .............. | H04N 13/139 348/47 |
| 2011/0279277 A1* | 11/2011 | Li-Chung | ............ | G06Q 10/109 340/573.7 |
| 2013/0041221 A1* | 2/2013 | McDowall | ......... | A61B 1/00096 600/111 |
| 2013/0113892 A1* | 5/2013 | Nakamaru | .............. | G03B 35/18 348/47 |
| 2015/0264333 A1* | 9/2015 | Ishiga | ............... | H01L 27/14623 382/154 |
| 2015/0297311 A1* | 10/2015 | Tesar | ..................... | G02B 21/16 600/411 |
| 2016/0029011 A1 | 1/2016 | Mizoguchi et al. | | |
| 2016/0249811 A1* | 9/2016 | Khan | ................. | A61B 1/00009 600/474 |
| 2016/0291348 A1* | 10/2016 | Chen | ..................... | G02C 11/10 |

FOREIGN PATENT DOCUMENTS

| | | |
|---|---|---|
| JP | 2004-305272 A | 11/2004 |
| JP | 2010-187250 A | 8/2010 |
| JP | 2010-279457 A | 12/2010 |
| JP | 2010-279507 A | 12/2010 |
| JP | 2013-244044 A | 12/2013 |
| WO | WO 2014/163109 A1 | 10/2014 |

* cited by examiner

CORRECTION PROCESSING OF A SURGICAL SITE IMAGE

TECHNICAL FIELD

The present technology relates to an image processing apparatus, an image processing method, a program, and a surgical system, and particularly relates to an image processing apparatus, an image processing method, a program, and a surgical system, capable of displaying an appropriate surgical site image, for example.

BACKGROUND ART

For example, Patent Document 1 discloses a technique of generating a reference image by reducing a medical image, calculating the displayable number of reference images in accordance with the monitor size, and arranging the displayable number of reference images on the display screen of the monitor to display the reference images in a uniform size regardless of the monitor size.

CITATION LIST

Patent Document

Patent Document 1: Japanese Patent Application Laid-Open No. 2004-305272

SUMMARY OF THE INVENTION

Problems to be Solved by the Invention

Meanwhile, the visibility of the image displayed on the monitor, that is, how the image quality is perceived differs depending on the viewing distance and the monitor size.

In a medical field, monitors are often installed within a predetermined range in a surgery room, for example, and thus, the monitor size greatly affects the visibility of the image displayed on the monitor.

For example, noise is more visible in a case of a large monitor size, and this sometimes leads to fatigue felt by a practitioner viewing the image displayed on the monitor.

Therefore, there is a demand for providing an image of image quality appropriate to the monitor size of the monitor displaying the image.

Furthermore, there is a demand in a medical field to display, for a practitioner or the like, an appropriate surgical site image as a captured surgical site with good visibility on a monitor as a display apparatus to display the surgical site image.

The present technology has been made in view of such a situation and aims to be able to display an appropriate surgical site image.

Solutions to Problems

An image processing apparatus or a program according to an embodiment of the present technology is an image processing apparatus including a control unit that controls to perform correction processing on a surgical site image as a captured surgical site on the basis of information related to display of a display apparatus that displays the surgical site image, or a program that causes a computer to function as the image processing apparatus.

An image processing method according to an embodiment of the present technology is an image processing method including controlling execution of correction processing on the surgical site image including a surgical site on the basis of information related to display of a display apparatus that displays a surgical site image.

A surgical system according to an embodiment of the present technology is a surgical system including: an endoscope configured to photograph an image; a control unit configured to control to perform correction processing on a surgical site image as a captured surgical site photographed by the endoscope on the basis of information related to display of a display apparatus that displays the surgical site image; and the display apparatus configured to display a corrected surgical site image that has undergone the correction processing.

The image processing apparatus, the image processing method, the program, and the surgical system according to an embodiment of the present technology performs control of executing correction processing on a surgical site image as a captured surgical site on the basis of information related to display of a display apparatus that displays the surgical site image.

Note that the image processing apparatus may be a separate apparatus or may be an internal block included in one apparatus.

Moreover, the program can be provided by transmission via a transmission medium, or by being recorded on a recording medium.

Effects of the Invention

According to an embodiment of the present technology, it is possible to display an appropriate surgical site image.

Note that effects described herein are non-restricting. The effects may be any effects described in the present disclosure.

MODE FOR CARRYING OUT THE INVENTION

<Endoscopic Surgical System According to One Embodiment of Present Technology>

Figure 1:
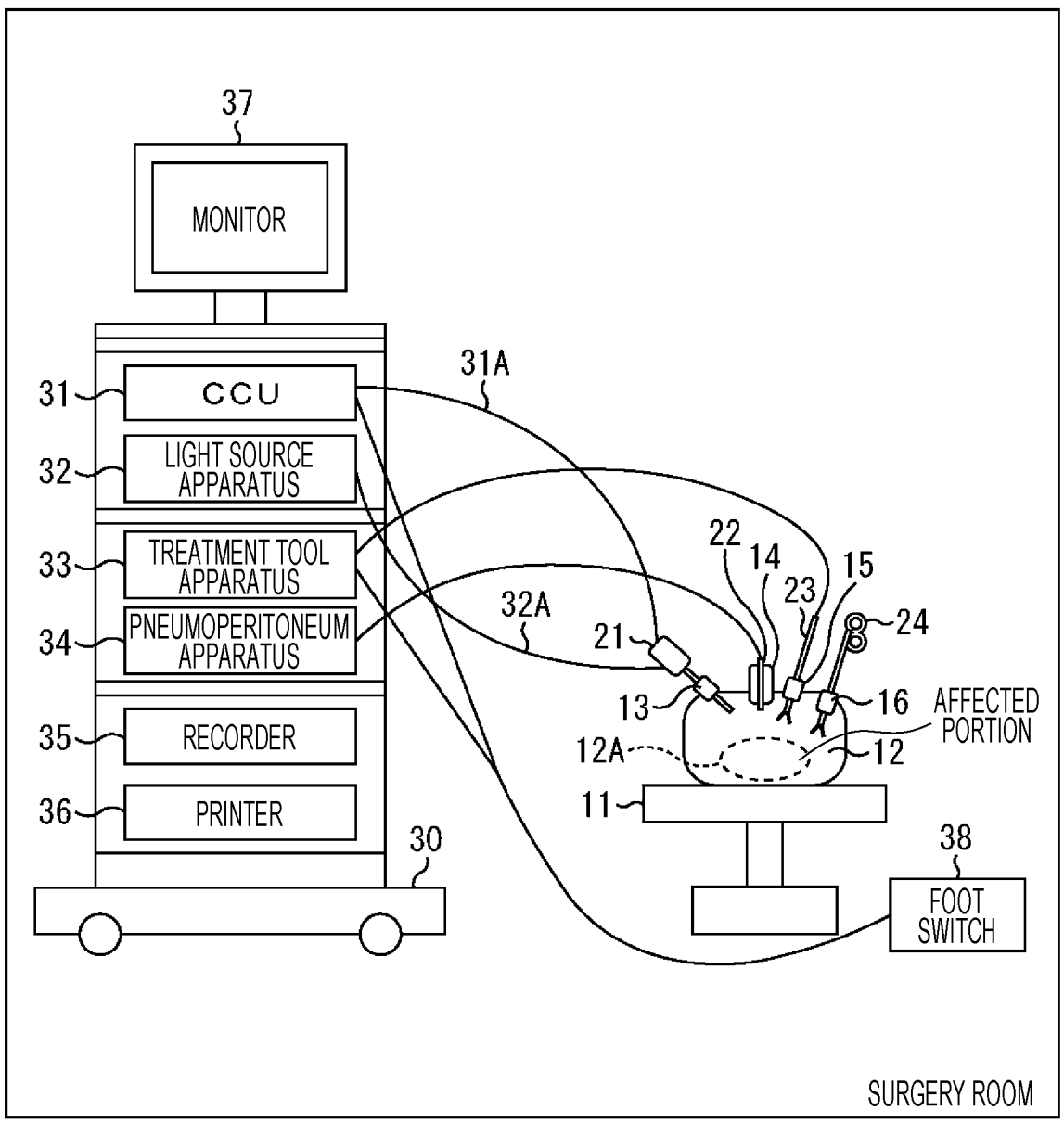
FIG. 1 is a diagram illustrating an endoscopic surgical system according to an embodiment of the present technology.

FIG. 1 is a diagram illustrating an endoscopic surgical system according to an embodiment of the present technology.

The endoscopic surgical system illustrated in FIG. 1 is installed in a surgery room and the endoscopic surgical system is used in an abdominal surgery or the like with an endoscopic surgery in place of a conventional laparotomy surgery, for example.

In FIG. 1, a patient bed 11 is arranged in a surgery room, with a patient 12 lying on the patient bed 11.

Trocars 13, 14, 15, and 16 as puncture tools are attached to the patient 12 through several small holes (four positions in FIG. 1) formed in the abdominal wall, instead of conventional laparotomy of cutting and opening the abdominal wall.

The trocars 13 to 16 have through holes (not illustrated) through which surgical tools (for example, endoscopes, energy treatment tools such as electric scalpels, forceps, and the like) used in surgery are inserted to the patient 12. In FIG. 1, an endoscope 21 is inserted via the trocar 13, a pneumoperitoneum needle 22 is inserted via the trocar 14, an energy treatment tool 23 is inserted via the trocar 15, and forceps 24 inserted via the trocar 16. The endoscope 21, the energy treatment tool 23, and the forceps 24 are individually held by, for example, a practitioner, an assistant, a scope specialist, a robot, or the like.

In FIG. 1, the endoscopic surgical system includes the endoscope 21, the pneumoperitoneum needle 22, the energy treatment tool 23, the forceps 24, a cart 30, a camera control unit (CCU) 31, a light source apparatus 32, a treatment tool apparatus 33, a pneumoperitoneum apparatus 34, a recorder 35, a printer 36, a monitor 37, and a foot switch 38.

With this endoscopic surgical system, the monitor 37 displays a surgical site image that captured an affected portion (tumor or the like) 12A as a surgical site being a surgery target captured as a video image by the endoscope 21. While viewing in real time the surgical site image displayed on the monitor 37, the practitioner performs treatment such as resection of the affected portion 12A with the energy treatment tool 23, or the like.

The endoscope 21 includes a camera (photographing apparatus), specifically, a camera head including an image sensor or the like, and an observation optical system (none is illustrated), and photographs an image.

That is, in FIG. 1, the endoscope 21 is a laparoscope and illuminates the affected portion 12A, surroundings of the affected portion 12A, and the like by emitting light supplied from the light source apparatus 32 via a light guide cable 32A.

Furthermore, the endoscope 21 receives the reflected light of the light emitted by the endoscope 21 with the image sensor of the camera head through the observation optical system, so as to photograph the surgical site image as a captured surgical site such as the affected portion 12A.

Then, the endoscope 21 supplies the surgical site image to the CCU 31 via a camera cable 31A.

The pneumoperitoneum needle 22 is a needle that delivers a gas (for example, air, carbon dioxide gas, and the like) supplied from the pneumoperitoneum apparatus 34 to the abdomen such as the vicinity of the affected portion 12A in the body of the patient 12 and that sucks the gas inside the patient 12 to the pneumoperitoneum apparatus 34.

The energy treatment tool 23 is a surgical tool using electrical energy, for example, an electric scalpel that cuts the affected portion 12A by electric heat, or the like.

The forceps 24 is a surgical tool that grips tissues or the like in a living body.

Apparatuses as medical devices included in the endoscopic surgical system are mounted on the cart 30 as needed. In FIG. 1, the CCU 31 or the monitor 37 is mounted on the cart 30.

The CCU 31 controls the camera head of the endoscope 21 via the camera cable 31A, so as to adjust, for example, focusing, an aperture, exposure time, or the like.

Furthermore, the CCU 31 performs control of various types of processing so as to perform correction processing on the surgical site image from the endoscope 21 on the basis of information related to the display of the monitor 37 as a display apparatus that displays the image (surgical site image or the like) supplied from the endoscope 21 via the camera cable 31A.

Then, the CCU 31 supplies a processed image (corrected surgical site image, or the like) obtained by performing (applying) an image processing as correction processing on the image (surgical site image, or the like) supplied from the endoscope 21 via the camera cable 31A, to the monitor 37.

Note that while FIG. 1 illustrates a case where the endoscope 21 is connected with the CCU 31 via the wired camera cable 31A, the endoscope 21 and the CCU 31 can be connected wirelessly, instead.

The light source apparatus 32 is connected to the endoscope 21 via the light guide cable 32A. The light source apparatus 32 switches and emits light of various wavelengths as necessary, and supplies the light to the endoscope 21 via the light guide cable 32A.

The treatment tool apparatus 33 is a high-frequency output apparatus that supplies a high frequency current to the energy treatment tool 23.

The pneumoperitoneum apparatus 34 has an air supply means and an air suction means (none is illustrated), and performs air supply and suction via the pneumoperitoneum needle 22.

The recorder 35 records a surgical site image or the like photographed by the endoscope 21.

The printer 36 prints a surgical site image or the like photographed by the endoscope 21.

The monitor 37 is a display apparatus including a liquid crystal display (LCD), an organic electro luminescence (EL) panel, and the like so as to display an image supplied from the CCU 31, for example.

The foot switch 38 is operated by a foot by, for example, a practitioner, an assistant, or the like, and supplies an operation signal (trigger signal) corresponding to the foot operation to the CCU 31 and the treatment tool apparatus 33, so as to control the CCU 31 and the treatment tool apparatus 33.

Note that the camera included in the endoscope 21 may be a monocular camera (single-view camera) or a multi-view camera of two or more eyes such as a stereo camera. In a case where a multi-view camera such as a stereo camera is adopted as the camera of the endoscope 21, it is possible to display a three-dimensional (3D) image as a surgical site image on the monitor 37.

Moreover, while FIG. 1 illustrates a case where one monitor 37 is provided as a monitor that displays a surgical site image, it is possible to provide a plurality of monitors, that is, one or more monitors in addition to the monitor 37 as monitors to display the surgical site image.

In a case where a plurality of monitors is provided as the monitor that displays the surgical site image, the monitor sizes of the plurality of monitors may be equal to or different from each other.

Furthermore, it is possible to display a same image photographed by the endoscope 21 on the plurality of monitors.

Moreover, in a case where the plurality of monitors is provided, it is possible to provide a plurality of endoscopes so as to display separate images photographed by the individual endoscopes on individual monitors.

Furthermore, it is possible to display different images such as a wide-view image or a zoom-up (enlarged) image of an image photographed by the endoscope 21 on a plurality of monitors.

<First Configuration Example of CCU 31>

Figure 2:
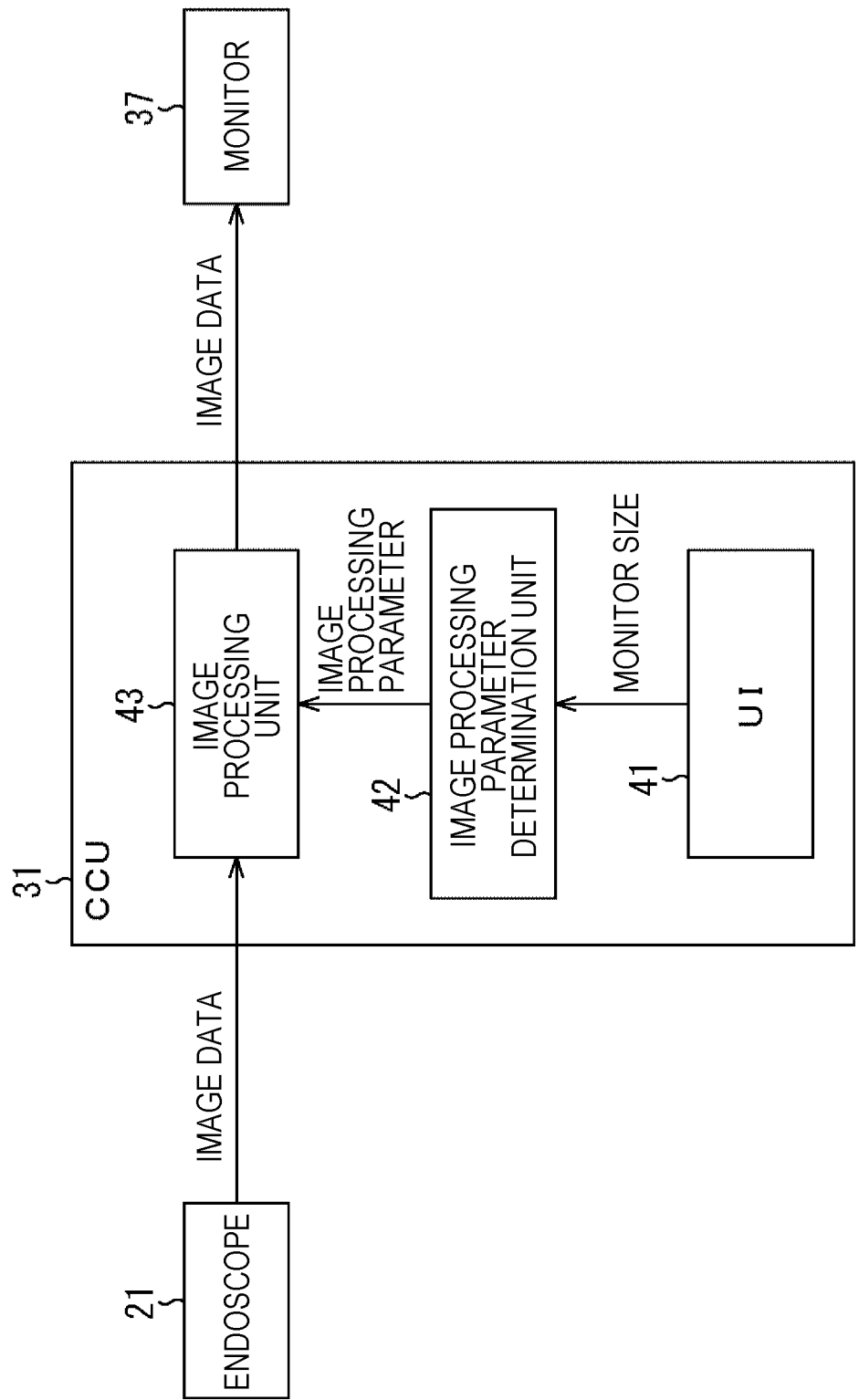
FIG. 2 is a block diagram illustrating a first configuration example of a CCU 31.

FIG. 2 is a block diagram illustrating a first configuration example of the CCU 31 in FIG. 1.

In FIG. 2, the CCU 31 includes a user interface (UI) 41, an image processing parameter determination unit 42, and an image processing unit 43.

The UI 41 is operated by, for example, a practitioner, an assistant, a scope specialist, or the like as a user of the endoscopic surgical system of FIG. 1. The user can input the monitor size of the monitor 37 by operating the UI 41. The UI 41 supplies the monitor size input by the user's operation to the image processing parameter determination unit 42.

The image processing parameter determination unit 42 obtains the monitor size from the UI 41. The image processing parameter determination unit 42 determines an image processing parameter to be used for image processing by the image processing unit 43 in accordance with the monitor size from the UI 41 and supplies the determined parameter to the image processing unit 43.

The image processing unit 43 receives the image processing parameter supplied from the image processing parameter determination unit 42, and together with this, receives a surgical site image as a captured surgical site (image data thereof) supplied from the endoscope 21.

The image processing unit 43 uses the image processing parameter from the image processing parameter determination unit 43 to perform correction processing on a surgical site image as image processing on a surgical site image from the endoscope 21, so as to perform image processing corresponding to the monitor size of the monitor 37 that displays a surgical site image that has undergone the image processing (correction processing), onto the surgical site image. Then, the image processing unit 43 supplies the surgical site image (image data thereof) that has undergone the image processing to the monitor 37 so as to display the image.

Figure 3:
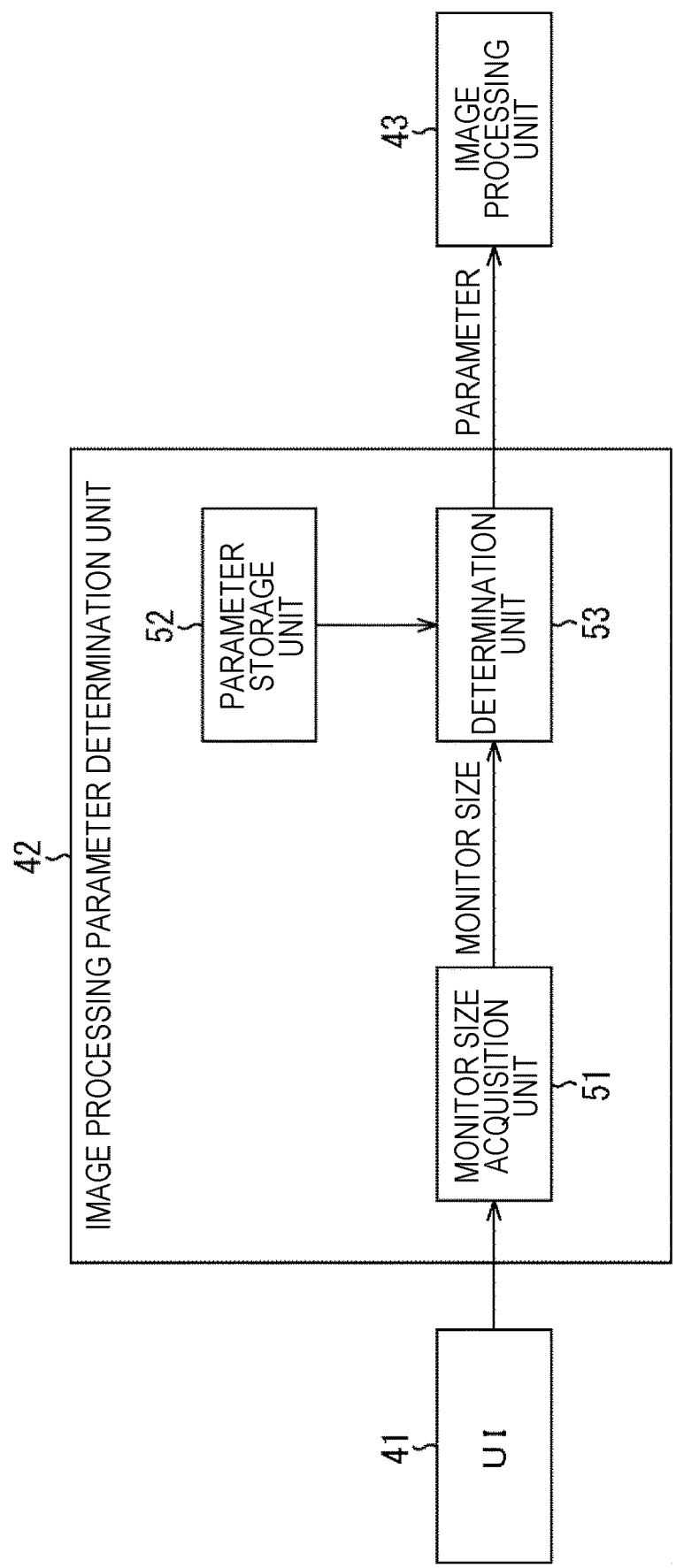
FIG. 3 is a block diagram illustrating a configuration example of an image processing parameter determination unit 42.

FIG. 3 is a block diagram illustrating a configuration example of the image processing parameter determination unit 42 of FIG. 2.

In FIG. 3, the image processing parameter determination unit 42 includes a monitor size acquisition unit 51, a parameter storage unit 52, and a determination unit 53.

The monitor size acquisition unit 51 obtains the monitor size supplied from the UI 41 in FIG. 2 and supplies it to the determination unit 53, for example.

The parameter storage unit 52 stores correction processing (information thereof) appropriate for displaying a surgical site image on each of monitors in association with information related to the display of various monitors such as the monitor 37 displaying a surgical site image.

That is, the parameter storage unit 52 stores a plurality of (sets of) image processing parameters as image processing parameters to be used in the image processing (correction processing) performed by the image processing unit 43 of FIG. 2 in association with the monitor size (information related to monitor display), for example.

The determination unit 53 determines an image processing parameter to be used for image processing by the image processing unit 43 from among the plurality of image processing parameters stored in the parameter storage unit 52 in accordance with the monitor size supplied from the monitor size acquisition unit 51, and supplies the determined parameter as a target parameter to the image processing unit 43.

Figure 4:
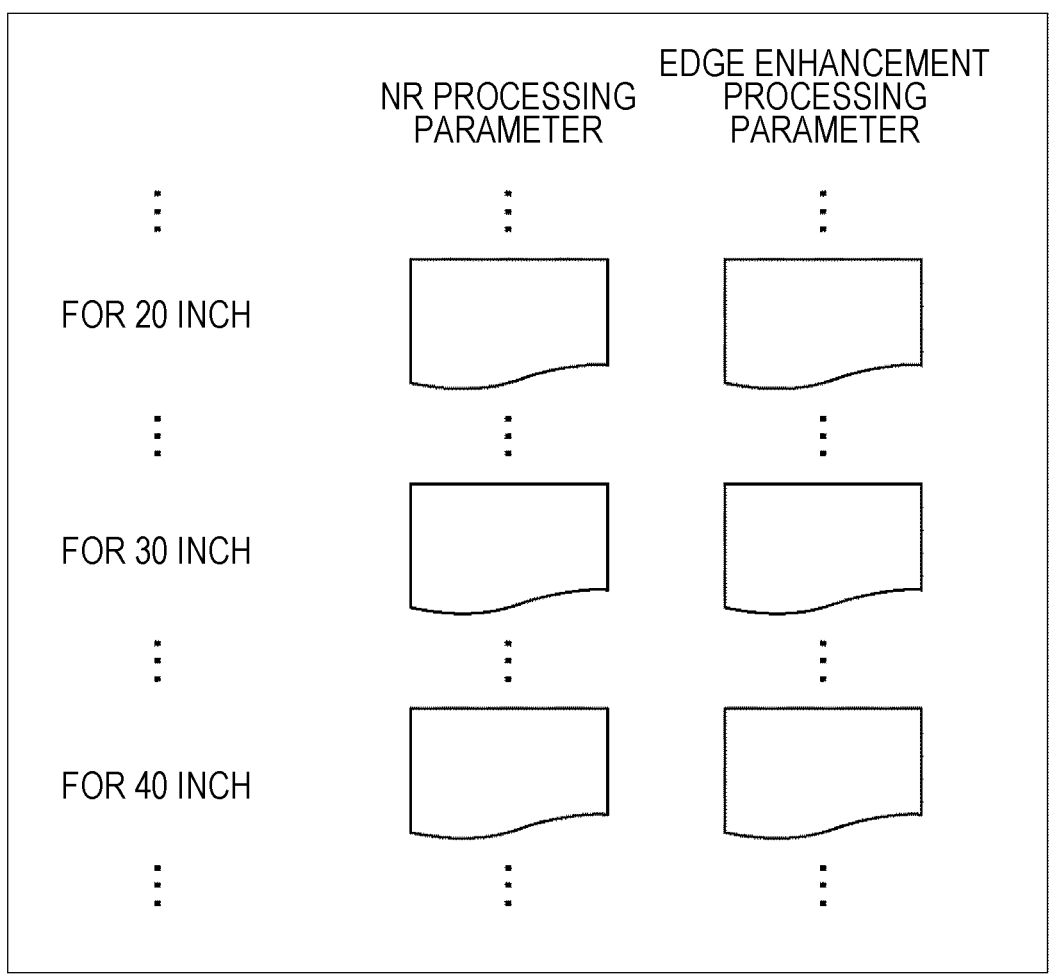
FIG. 4 is a diagram illustrating an example of storage of a plurality of image processing parameters in a parameter storage unit 52.

FIG. 4 is a diagram illustrating an example of storage of a plurality of image processing parameters in the parameter storage unit 52 of FIG. 3.

The parameter storage unit 52 stores image processing parameters appropriate for the monitor size in association with each of the plurality of monitor sizes.

Herein, examples of image processing performed by the image processing unit 43 in FIG. 2 include noise reduction (NR) processing for removing (reducing) noise of an image, enhancement processing of enhancing a certain portion of an image, and the like.

Examples of the enhancement processing include edge enhancement processing typified by unsharp mask processing or the like, band enhancement processing of enhancing a specific frequency band, and the like. Since doctors would prefer the image quality enhancing the frequency band somewhat lower than the high frequency band, the CCU 31 of the endoscopic surgical system performs band enhancement processing in some cases.

FIG. 4 illustrates an assumable case where the image processing performed by the image processing unit 43 is NR processing and edge enhancement processing, in which parameters for NR processing and parameters for edge enhancement processing are stored as image processing parameters.

Note that the parameter storage unit 52 can store parameters for band enhancement processing in place of parameters for NR processing or parameters for edge enhancement processing. Moreover, the parameter storage unit 52 can store parameters for band enhancement processing in addition to the parameters for NR processing and parameters for edge enhancement processing. Furthermore, that the parameter storage unit 52 can store any one of the parameters for NR processing, parameters for edge enhancement processing, and the parameters for band enhancement processing.

The type of the image processing parameter to be stored in the parameter storage unit 52 is determined in accordance with the type of image processing performed by the image processing unit 43. That is, in the case where the image processing unit 43 can perform image processing of, for example, one or more of NR processing, edge enhancement processing, and band enhancement processing, or the like, the parameter storage unit 52 stores parameters corresponding to the image processing performed in the image processing unit 43.

Moreover, the parameter storage unit 52 can store image processing parameters for all monitor sizes of the monitors connectable to the CCU 31. In this case, the determination unit 53 determines the image processing parameter associated with the monitor size of the monitor 37 among the plurality of image processing parameters stored in the parameter storage unit 52 as a target parameter to be used for image processing in the image processing unit 43.

Moreover, the parameter storage unit 52 can store image processing parameters for several (a plurality of) monitor sizes among all monitor sizes of monitors connectable to the CCU 31.

In this case, when there is an image processing parameter associated with the monitor size of the monitor 37 among the plurality of image processing parameters stored in the parameter storage unit 52, the determination unit 53 determines the image processing parameter associated with the monitor size of the monitor 37 as a target parameter.

Moreover, when there is no image processing parameter associated with the monitor size of the monitor 37 among the plurality of image processing parameters stored in the parameter storage unit 52, the determination unit 53 can determine the image processing parameter associated with the monitor size closest to the monitor size of the monitor 37 among the plurality of image processing parameters stored in the parameter storage unit 52, as the target parameter.

Note that, when there is no image processing parameter associated with the monitor size of the monitor 37 among the plurality of image processing parameters stored in the parameter storage unit 52, it is possible to use another method to determine the target parameter, for example, by interpolation using the plurality of image processing parameters stored in the parameter storage unit 52.

Note that the image processing performed by the image processing unit 43 is not limited to the NR processing, the edge enhancement processing, or the band enhancement processing.

Moreover, in order to simplify the explanation, it is assumed that the image processing unit 43 performs, for example, NR processing and edge enhancement processing as image processing.

Figure 5:
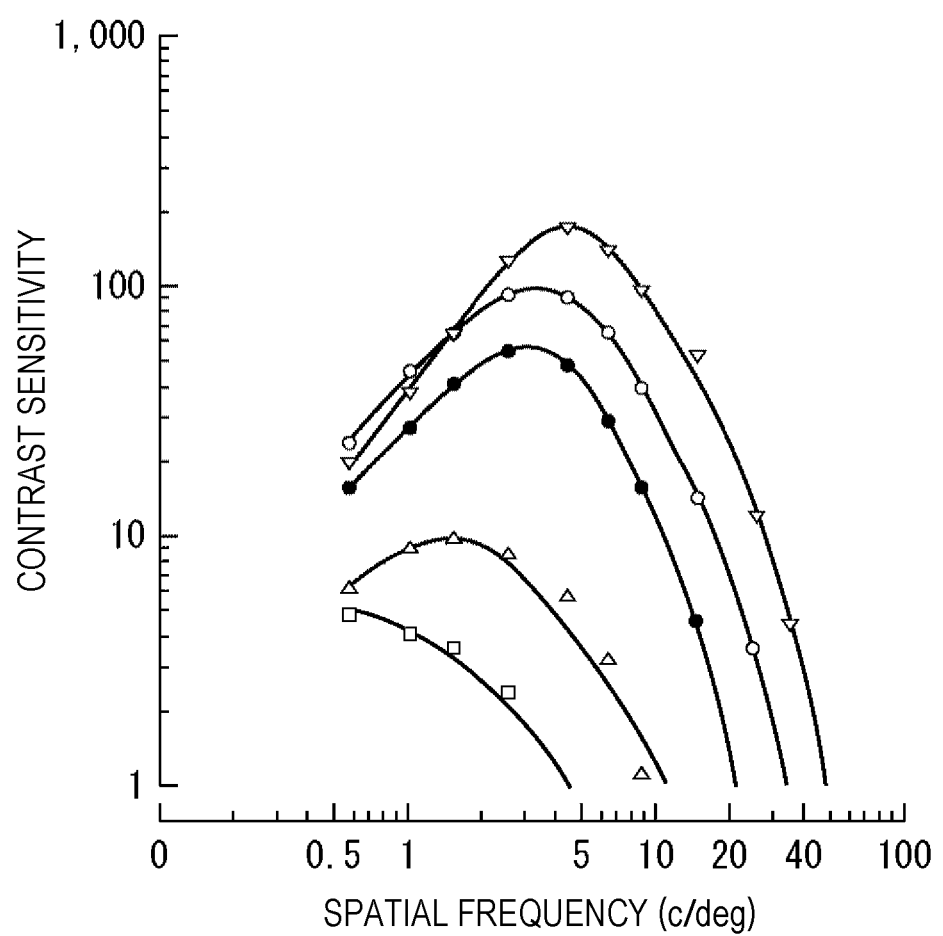
FIG. 5 is a diagram illustrating a relationship between a monitor size of a monitor and a contrast sensitivity to a contrast of an image displayed on the monitor.

FIG. 5 is a diagram illustrating a relationship between the monitor size of a monitor and contrast sensitivity to a contrast of an image displayed on the monitor.

Figure 6:
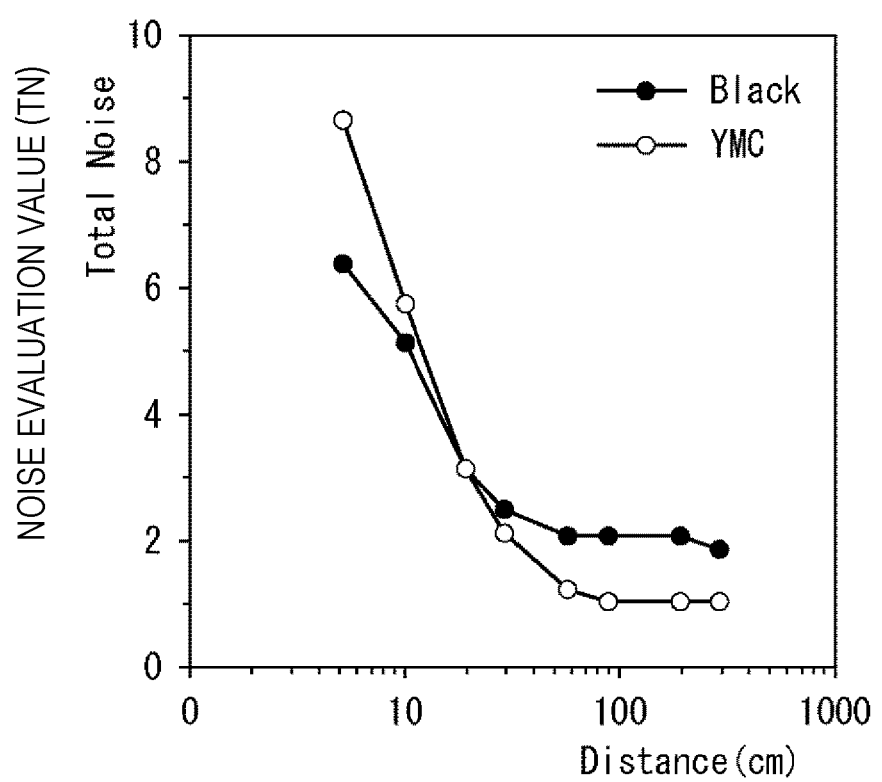
FIG. 6 is a diagram illustrating a relationship between the monitor size of a monitor and noise sensitivity to the noise of an image displayed on the monitor.

FIG. 6 is a diagram illustrating a relationship between the monitor size of a monitor and noise sensitivity (noise evaluation value) to the noise of an image displayed on the monitor.

Note that FIG. 5 is a citation from the conference of the Institute of Electronics, Information and Communication Engineers "Knowledge Base", Forest of Knowledge, Chapter 5 Frequency Characteristics of Visual System, from the Institute of Electronics, Information and Communication Engineers, 2010. FIG. 6 is a citation from Aoyama et.al, "An Evaluation Method for Image Noise of Various Output Devices" from Journal of the Society of Photography and Imaging of Japan 1964, p. 392.

Herein, a distance from a viewer of an image to the monitor that displays the image is referred to as a viewing distance.

Moreover, the degree of visibility of the noise in the image displayed on the monitor, that is, the degree of sensitivity of the viewer to the noise in the image displayed on the monitor is referred to as noise sensitivity.

Furthermore, the degree of sensitivity of the viewer to the contrast in the image displayed on the monitor is referred to as contrast sensitivity.

FIG. 5 illustrates a relationship between the spatial frequency (horizontal axis) of the monitor and the contrast sensitivity (vertical axis).

In a case where the viewing distance is fixed, as illustrated in FIG. 5, there is a tendency between the spatial frequency of the monitor and the contrast sensitivity that the higher the spatial frequency, the higher the contrast sensitivity, in a spatial frequency range of the monitor being a predetermined value (for example, about 10 c/deg (cycles/degree) or below.

The low spatial frequency of the monitor corresponds to the large monitor size, while the high spatial frequency of the monitor corresponds to the small monitor size.

Accordingly, for monitors having a monitor size corresponding to a predetermined spatial frequency, or above, there is a tendency that the smaller the monitor size (that is, that higher the spatial frequency), the higher the contrast sensitivity.

FIG. 6 illustrates a relationship between the viewing distance (horizontal axis) and the evaluation value (vertical axis) of noise representing noise visibility.

There is a tendency between the viewing distance and the evaluation value of the noise that the shorter the viewing distance, the greater the evaluation value of the noise.

The state that the viewing distance is short corresponds to the state that the monitor size is large with a constant viewing distance. In contrast, the state that the viewing distance is long corresponds to the state that the monitor size is small with a constant viewing distance. Furthermore, the evaluation value of the noise corresponds to the noise sensitivity representing the degree of sensitivity of the viewer to the noise in the image displayed on the monitor.

Therefore, there is a tendency that the larger the monitor size (the shorter the viewing distance), the higher the noise sensitivity.

From the above, the noise sensitivity and the contrast sensitivity have a relation that the noise sensitivity becomes dominant in a case where the monitor size is large, and the contrast sensitivity becomes dominant in a case where the monitor size is small.

Therefore, it is desirable to adjust the intensity of NR processing and edge enhancement processing as image processing of the image processing unit 43 as follows.

That is, the large monitor size would increase the noise sensitivity, facilitating visual recognition of the noise. Accordingly, desirable NR processing of the image processing unit 43 with the large monitor size would be to perform NR processing with high intensity so as to further reduce the noise.

Furthermore, the large monitor size indicates the large area per pixel of the monitor, leading to higher visibility of noise and ringing caused by edge enhancement processing and the like. Therefore, in a case where the monitor size is large, it is desirable to perform edge enhancement processing with a low intensity as edge enhancement processing of the image processing 43 so as to suppress the occurrence of ringing.

In contrast, the small monitor size would increase the contrast sensitivity, facilitating sensing of the high/low level of contrast. Therefore, in a case where the monitor size is small, it is desirable to perform edge enhancement processing with a high intensity as edge enhancement processing of the image processing unit 43 so as to increase the contrast to enhance visibility.

In addition, performing high intensity edge enhancement processing in a case where the monitor size is large might increase the contrast excessively, leading to an increase in the eye fatigue of the practitioner as a viewer of the surgical site image.

Therefore, the parameter storage unit 52 stores the parameters for NR processing in association with the monitor size so as to perform high intensity NR processing in a case where the monitor size is large, and to perform low intensity NR processing in a case where the monitor size is small.

Furthermore, the parameter storage unit 52 stores the parameters for edge enhancement processing in association with the monitor size so as to perform low intensity edge enhancement processing in a case where the monitor size is large, and perform high intensity edge enhancement processing in a case where the monitor size is small.

Figure 7:
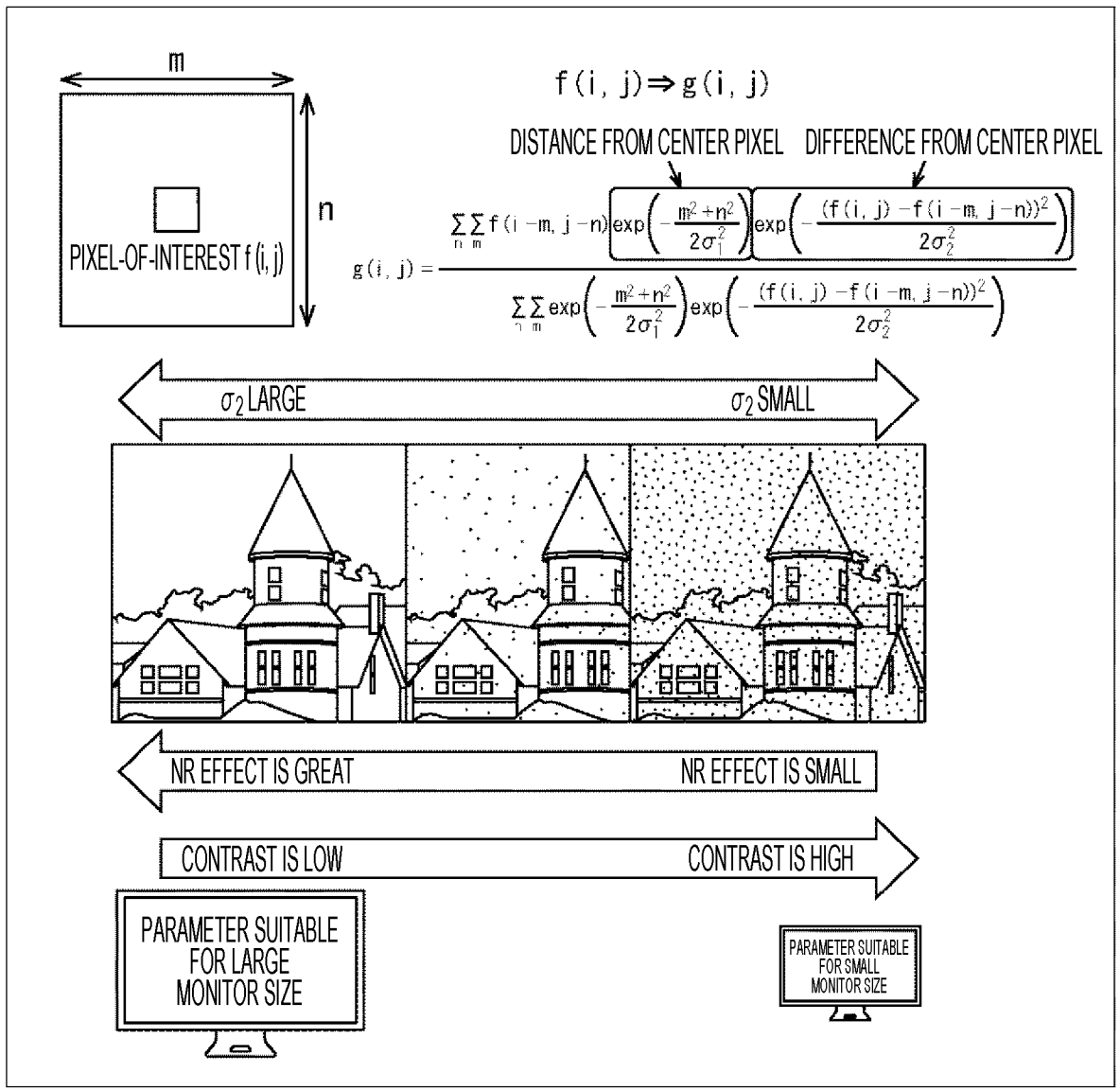
FIG. 7 is a diagram illustrating an example of NR processing.

FIG. 7 is a diagram illustrating an example of NR processing.

Filtering by a bilateral filter can be adopted in the NR processing, for example.

For example, when pixel the i-th from the left and j-th from the top of the surgical site image is defined as a target pixel, the pixel value of the target pixel before filtering by the bilateral filter is denoted by f (i, j) while the pixel value after filtering is denoted by g (i, j).

In this case, the filtering of the target pixel by the bilateral filter is performed by using the pixel values of m (horizontal)×n (vertical) pixels around the target pixel as a center in accordance with the expression illustrated in FIG. 7, so as to obtain the pixel value g (i, j) after filtering.

The expression of filtering by the bilateral filter includes parameters $\sigma_1^2$ and $\sigma_2^2$, and it is possible to adopt these $\sigma_1^2$ and $\sigma_2^2$ as the parameters for NR processing.

When the parameters $\sigma_1^2$ and $\sigma_2^2$ are increased, the intensity of NR processing (NR effect) is increased. When the parameters $\sigma_1^2$ and $\sigma_2^2$ are decreased, the intensity of NR processing (NR effect) is decreased.

Therefore, in a case where the filtering by the bilateral filter is adopted as the NR processing and the parameters $\sigma_1^2$ or $\sigma_2^2$ is adopted as the parameters for the NR processing, the image processing parameter determination unit 42 can determine the parameters as the target parameter used in the NR processing such that the larger the monitor size, the greater the values of the parameters $\sigma_1^2$ or $\sigma_2^2$.

Note that the contrast of the image after filtering by the bilateral filter is lower than the contrast of the image before filtering (original image). The higher the intensity of NR processing, the greater the degree of reduction in contrast.

Accordingly, filtering by the bilateral filter can be regarded as both NR processing of removing noise, and contrast reduction processing of reducing the contrast or edge suppression processing of suppressing edges.

In the case where filtering by the bilateral filter is regarded as contrast reduction processing or edge suppression processing, the image processing unit 43 is considered to perform processing such that the larger the monitor size, the higher the intensity of the contrast reduction processing or the edge suppression processing.

Figure 8:
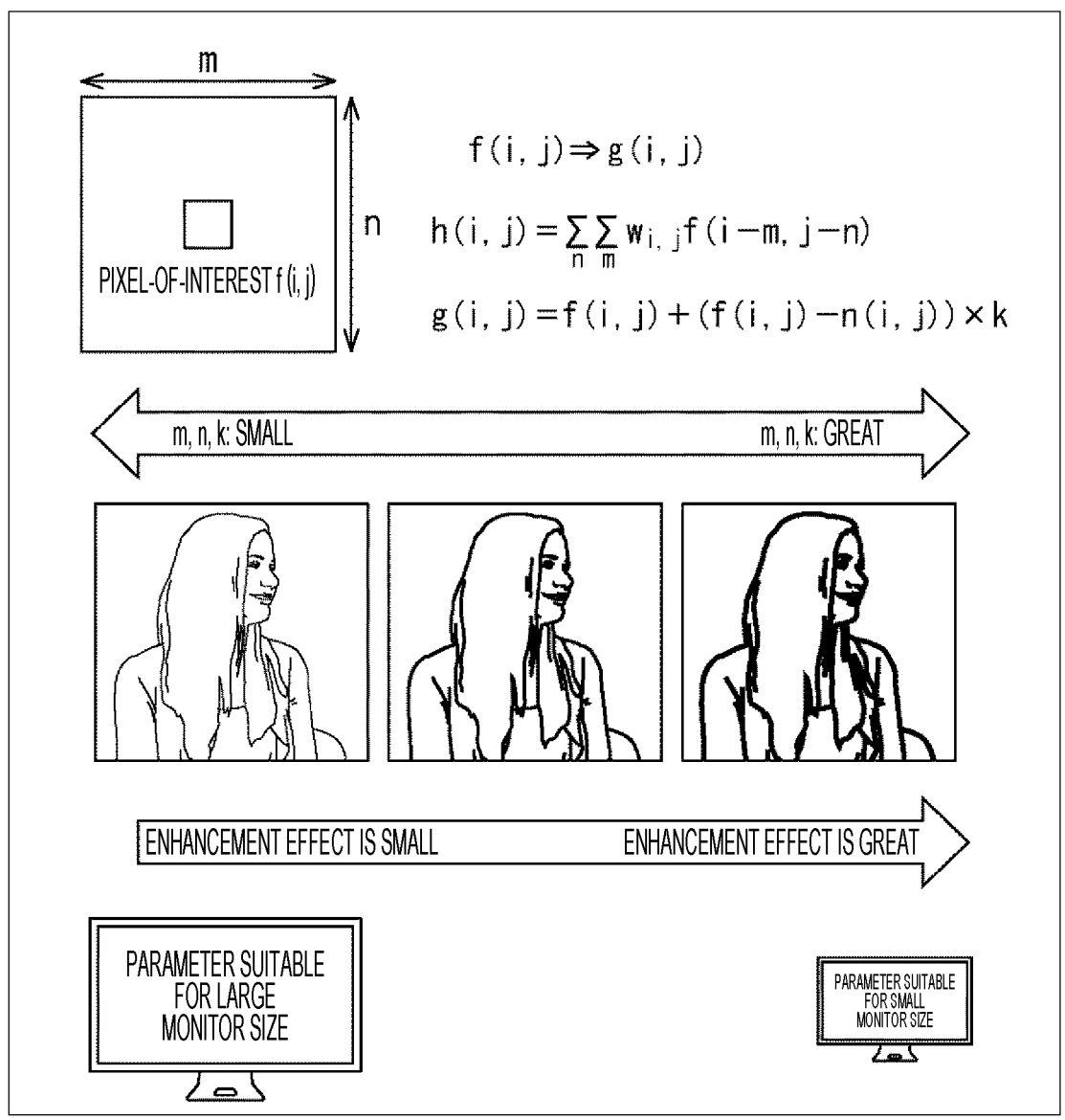
FIG. 8 is a diagram illustrating an example of edge enhancement processing.

FIG. 8 is a diagram illustrating an example of edge enhancement processing.

Unsharp mask processing can be adopted as the edge enhancement processing, for example.

Herein, the pixel value of the target pixel before unsharp mask processing is denoted by f (i, j), and the pixel value after unsharp mask processing is denoted by g (i, j).

In this case, the unsharp mask processing is performed by using the pixel values of m (horizontal)×n (vertical) pixels around the target pixel as a center in accordance with the expression illustrated in FIG. 8, so as to obtain the pixel value g (i, j) after the unsharp mask processing.

The expression as the unsharp mask processing includes parameters k, m, n, and these parameters k, m, and n can be adopted as parameters for edge enhancement processing.

Increasing the parameter k, m, or n would increase the intensity (enhancement effect) of the edge enhancement processing, while decreasing the parameter k, m, or n would decrease the intensity of the edge enhancement processing.

Therefore, in a case where the filtering by the unsharp mask processing is adopted as the edge enhancement processing and the parameter k, m, or n is adopted as the parameter for the edge enhancement processing, the image processing parameter determination unit 42 can determine the parameter as the target parameter used in the edge enhancement processing such that the smaller the monitor size, the greater the value of the parameter k, m, or n.

Figure 9:
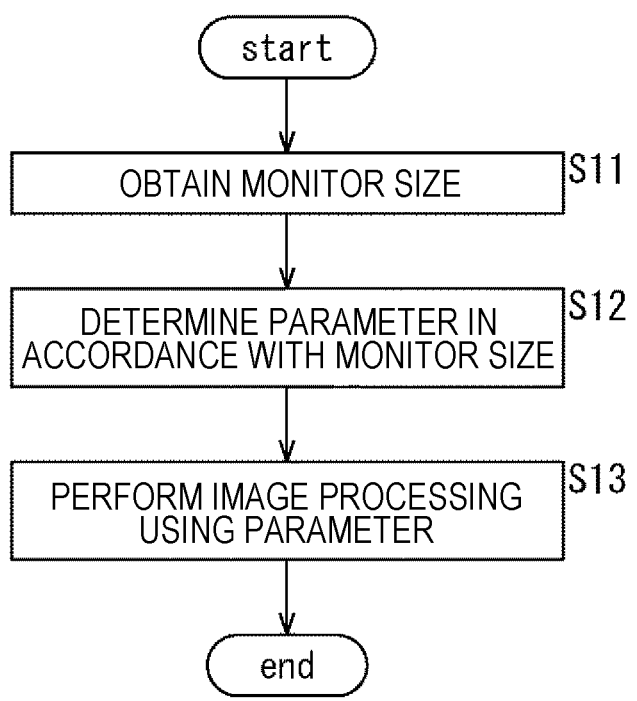
FIG. 9 is a flowchart illustrating an example of the processing of the CCU 31.

FIG. 9 is a flowchart illustrating an example of the processing of the CCU 31 in FIG. 2.

In step S11, the image processing parameter determination unit 42 waits for an input of monitor size of the monitor 37 by a user such as a practitioner by operation on the UI 41, and then obtains the monitor size, and thereafter the processing proceeds to step S12.

In step S12, the image processing parameter determination unit 42 determines the image processing parameter to be used for image processing in the image processing unit 43 as a target parameter in accordance with the monitor size obtained from the UI 41, and supplies the parameter to the image processing unit 43 and then, the processing proceeds to step S13.

In step S13, the image processing unit 43 performs image processing on the surgical site image supplied from the endoscope 21 using the image processing parameter as the target parameter from the image processing parameter determination unit 43, so as to perform image processing corresponding to the monitor size of the monitor 37 on the surgical site image. Then, the image processing unit 43 supplies the surgical site image that has undergone the image processing to the monitor 37 so as to display the image.

As described above, the endoscopic surgical system illustrated in FIG. 1 has a configuration in which the image processing unit 43 performs image processing having intensity corresponding to the monitor size of the monitor 37 on the surgical site image. With this configuration, it is possible to supply a surgical site image with image quality appropriate for the monitor size of the monitor 37.

That is, in a case where the monitor size is large, for example, NR processing with high intensity is performed and edge enhancement processing with low intensity is performed. Moreover, in a case where the monitor size is small, for example, NR processing with low intensity is performed and edge enhancement processing with high intensity is performed.

Therefore, it is possible to suppress the reduction in the visibility of the surgical site image due to conspicuous noise and ringing in a case where the monitor size is large. Furthermore, it is possible to increase the contrast of the surgical site image to enhance the visibility in a case where the monitor size is small.

As a result, it is possible to reduce accumulation of fatigue on the practitioner due to viewing the surgical site image in a long surgery, for example.

Note that the intensity of the image processing by the image processing unit 43, that is, the image processing parameter can be determined in consideration of the viewing distance (distance between the monitor 37 and the practitioner or the like, viewing the surgical site image displayed on the monitor 37) in addition to the monitor size.

For example, it is possible to store in the parameter storage unit 52 of the image processing parameter determination unit 42 (FIG. 3) a plurality of image processing parameters suitable for a plurality of monitor sizes with respect to a certain distance set as a standard viewing distance. In this case, the determination unit 53 can obtain an image processing parameter corresponding to the monitor size of the monitor 37 from among the plurality of image processing parameters stored in the parameter storage unit 52, and can correct the image processing parameter in accordance with a difference between an actual viewing distance and the standard viewing processing.

Alternatively, it is possible to allow the parameter storage unit 52 to store image processing parameters appropriate for individual combinations of each of the plurality of viewing distances and each of the plurality of monitor sizes. In this case, the determination unit 53 can obtain the image processing parameter corresponding to the actual viewing distance and the monitor size of the monitor 37 from among the plurality of image processing parameters stored in the parameter storage unit 52.

The viewing distance can be input by the user by operating on the UI 41 or it is also possible to use a monitor photographing distance to be described below as the viewing distance, for example.

Furthermore, the image processing parameter for performing image processing with appropriate intensity for each of the monitor sizes (and viewing distances) can be obtained by simulation, experiment, or the like, for example.

Note that, in a case where the monitor size is a predetermined lower limit value or below, the intensity of the image processing of the image processing unit 43 (namely, the image processing parameter) can be fixed to the intensity corresponding to the lower limit value. Similarly, in a case where the monitor size is a predetermined upper limit value or above, the intensity of the image processing of the image processing unit 43 can be fixed to the intensity corresponding to the upper limit value.

In addition, the image processing parameters can be set for individual users. That is, for example, it is possible for a certain user A to use the image processing parameter associated with the monitor size of the monitor 37 in the parameter storage unit 52, and for the other user B to use an image processing parameter associated with a monitor size or the like of a size one step higher or one step lower than the monitor size of the monitor 37 in the parameter storage unit 52.

While the above is an exemplary case where the CCU 31 performs the image processing as the correction processing for the surgical site image in accordance with the monitor size (the display screen size), the correction processing for the surgical site image can be performed not merely in accordance with the monitor size but also can be performed in accordance with (on the basis of) information related to the display of the monitor 37 (hereinafter, also referred to as display related information) as a display apparatus that displays a surgical site image.

Besides the monitor size, for example, the display related information includes brightness of the monitor 37 (image displayed on the monitor 37), resolution (display resolution), and the like.

The higher the brightness of the monitor 37, the lower the visibility of the pixel difference. Therefore, in a case where the brightness of the monitor 37 is high, it is possible to reduce the intensity of the NR processing and increase the intensity of the edge enhancement processing. In contrast, in a case where the brightness of the monitor 37 is low, it is possible to increase the intensity of the NR processing and reduce the intensity of the edge enhancement processing.

The brightness of the monitor 37 can be obtained from other setting information of the metadata set on the monitor 37 or can be obtained using an illuminance sensor, for example.

The resolution of the monitor 37 is set such that the higher the resolution, the lower the visibility of one pixel. Therefore, in a case where the resolution of the monitor 37 is high, it is possible to reduce the intensity of the NR processing and increase the intensity of the edge enhancement processing. In contrast, in a case where the resolution of the monitor 37 is low, it is possible to increase the intensity of the NR processing and decrease the intensity of the edge enhancement processing.

The resolution of the monitor 37 can be obtained from the setting information set on the monitor 37, for example.

Furthermore, the correction processing performed onto the surgical site image in the CCU 31 can be performed on the basis of the display related information of the monitor 37, the display related information, and the usage conditions of the monitor 37.

The usage conditions of the monitor 37 include the brightness of the installation location of the monitor 37, the viewing distance, the viewing time, and the like of a user viewing (browsing) the monitor 37 (or the image displayed on the monitor 37).

For example, the longer the viewing time (surgery time) becomes, the more the user viewing the monitor 37 tends to feel fatigue. Therefore, the CCU 31 can change the intensity of the NR processing or the edge enhancement processing as the correction processing in accordance with the display related information, the viewing time as the usage conditions of the monitor 37, or the length of the estimated surgery time.

For example, the CCU 31 makes it possible to set such that the longer the length of the viewing time or the estimated surgery time, the higher the intensity of the NR processing and the smaller the intensity of the edge enhancement processing. Furthermore, the CCU 31 makes it possible to set such that the shorter the length of the viewing time or the estimated surgery time, the smaller the intensity of the NR processing and the higher the intensity of the edge enhancement processing.

In addition, in the surgery room, the brighter the installation location of the monitor 37, for example, the brighter the shadowless lamp brightness is, the lower the visibility of the pixel difference for the user viewing the monitor 37. Therefore, the CCU 31 can change the intensity of the NR processing or the edge enhancement processing as the correction processing in accordance with the display related information and the brightness of the shadowless lamp as the usage conditions of the monitor 37.

For example, it is possible to set the CCU 31 such that the higher the brightness of the shadowless lamp, the lower the intensity of the NR processing or higher the intensity of the edge enhancement processing. Furthermore, it is possible to set the CCU 31 such that the lower the brightness of the shadowless lamp, the higher the intensity of the NR processing or lower the intensity of the edge enhancement processing.

The brightness of the shadowless lamp can be detected by a luminometer, for example.

Note that in a case where the correction processing on the surgical site image is performed in the CCU 31 on the basis of the display related information of the monitor 37 and on the basis of the usage conditions of the monitor 37, it is possible to consider the display related information of the monitor 37 and the usage conditions of the monitor 37 with equal weights or with different weights.

In addition to the above-described NR processing (contrast reduction processing), edge enhancement processing, and band enhancement processing as the image processing as correction processing onto the surgical site image, it is possible to adopt, for example, contrast adjustment processing of adjusting the contrast by tone curve correction and histogram smoothing, parallax adjustment processing of adjusting the parallax of a stereoscopic image, and the like.

The contrast adjustment processing can be performed, for example, such that the larger the monitor size, the lower the contrast adjustment processing intensity (processing of setting the contrast not too high, or reduce the contrast) and that the smaller the monitor size, higher the contrast adjustment processing intensity.

The parallax adjustment processing can be performed in a case where the surgical site image is a stereoscopic image, for example, such that the larger the monitor size, the lower the parallax adjustment processing intensity (processing of setting the parallax not too high, or reduce the parallax) and that the smaller the monitor size, higher the parallax adjustment processing intensity.

In the following description, for simplicity of explanation, explanation will be given with an exemplary case where monitor size is used as display related information and NR processing and edge enhancement processing are used as correction processing.

<Second Configuration Example of CCU 31>

Figure 10:
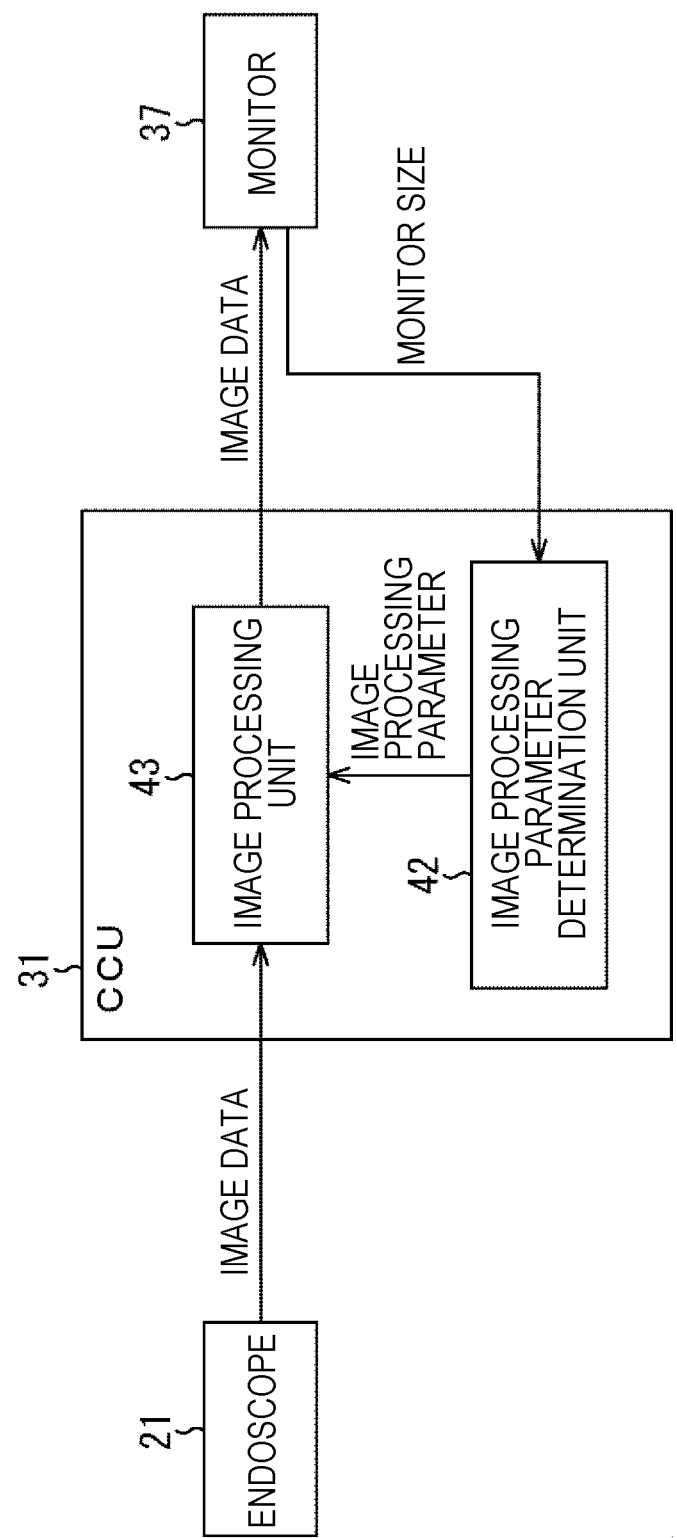
FIG. 10 is a block diagram illustrating a second configuration example of the CCU 31.

FIG. 10 is a block diagram illustrating a second configuration example of the CCU 31 in FIG. 1.

Note that in the figure, portions corresponding to the case of FIG. 2 are denoted by the same reference numerals, and the description thereof will be omitted as appropriate below.

In FIG. 10, the CCU 31 includes the image processing parameter determination unit 42 and the image processing unit 43.

Accordingly, the CCU 31 of FIG. 10 has a configuration similar to the case of FIG. 2 in that it includes the image processing parameter determination unit 42 and the image processing unit 43 and differs from the case of the FIG. 2 in that the UI 41 is not provided.

In the CCU 31 of FIG. 10, however, the monitor size acquisition unit 51 in the image processing parameter determination unit 42 (FIG. 3) communicates with the monitor 37 to obtain the monitor size of the monitor 37 from the monitor 37.

That is, in FIG. 10, the monitor 37 stores the monitor size of the monitor 37 as metadata. The monitor 37 performs wired communication or wireless communication with the monitor size acquisition unit 51 of the image processing parameter determination unit 42 to transmit the monitor size as metadata to the monitor size acquisition unit 51.

The monitor size acquisition unit 51 receives and thereby obtains the monitor size transmitted as metadata from the monitor 37 and supplies it to the determination unit 53 (FIG. 3).

As described above, in a case where the monitor size acquisition unit 51 communicates with the monitor 37 to obtain the monitor size of the monitor 37, for example, it is possible to omit user's (practitioner's or the like) input of the monitor size.

<Third Configuration Example of CCU 31>

Figure 11:
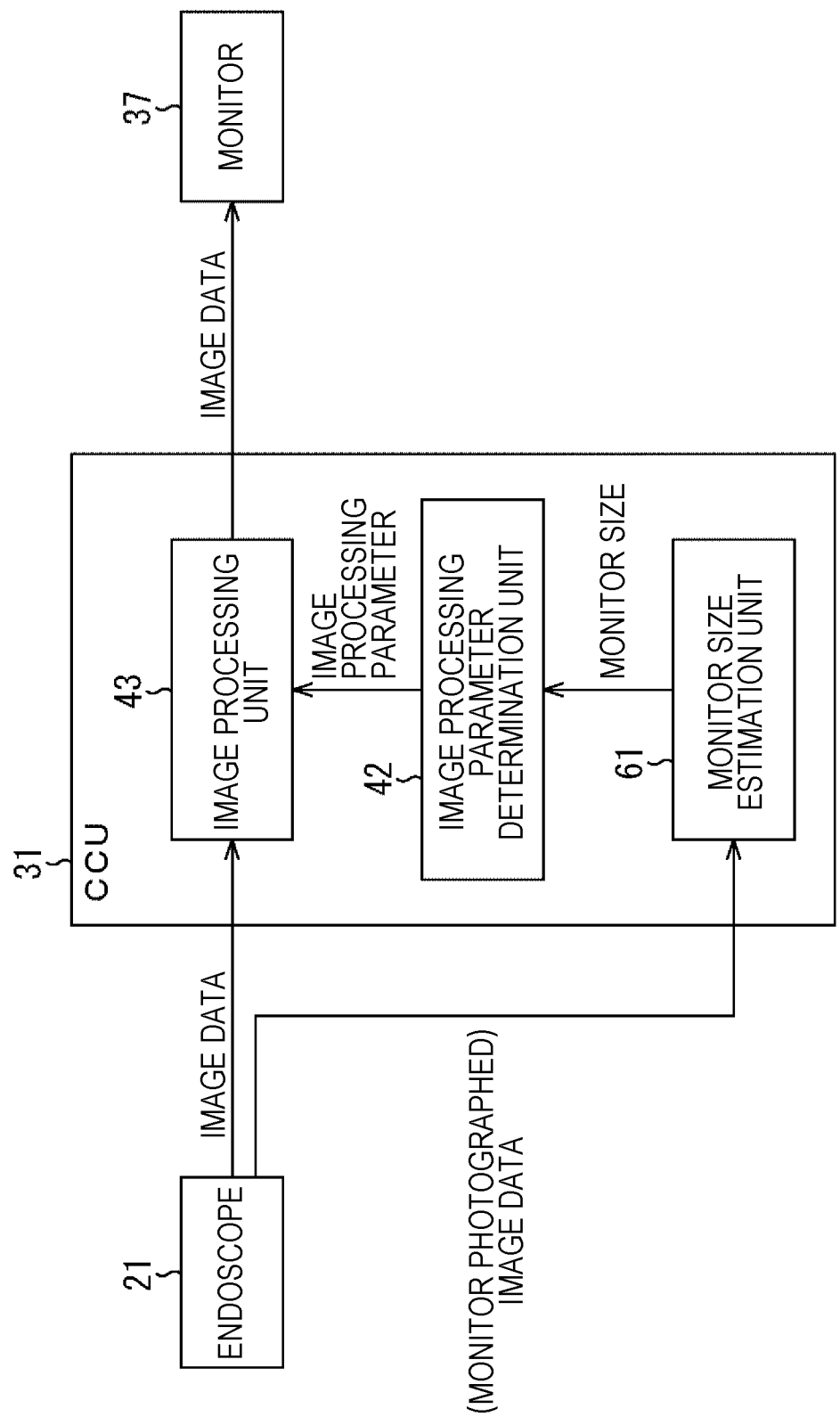
FIG. 11 is a block diagram illustrating a third configuration example of the CCU 31.

FIG. 11 is a block diagram illustrating a third configuration example of the CCU 31 in FIG. 1.

Note that in the figure, portions corresponding to the case of FIG. 2 are denoted by the same reference numerals, and the description thereof will be omitted as appropriate below.

In FIG. 11, the CCU 31 includes the image processing parameter determination unit 42, the image processing unit 43, and a monitor size estimation unit 61.

Accordingly, the CCU 31 of FIG. 11 has a configuration similar to the case of FIG. 2 in that it includes the image processing parameter determination unit 42 and the image processing unit 43 and differs from the case of the FIG. 2 in that the monitor size estimation unit 61 is provided in place of the UI 41.

A monitor photographed image (image data thereof) obtained by photographing the monitor 37 is supplied to the monitor size estimation unit 61.

Note that photographing of the monitor 37 can be performed by an arbitrary apparatus having a photographing function. Since the endoscopic surgical system illustrated in FIG. 1 includes the endoscope 21 having a photographing function, there is no need to separately prepare an apparatus having a photographing function (although it may be prepared), photographing of the monitor 37 can be performed by the endoscope 21.

The user such as a practitioner photographs the monitor 37 with the endoscope 21 before the start of surgery, for example. The monitor photographed image obtained by photographing the monitor 37 with the endoscope 21 is supplied to the monitor size estimation unit 61.

Note that the monitor photographed image can be photographed by a camera other than the endoscope 21, that is, for example, a camera installed in a surgery room such as a surgical field camera or the like.

The monitor size estimation unit 61 estimates the monitor size of the monitor 37 captured in the monitor photographed image on the basis of the monitor photographed image supplied from the endoscope 21 and supplies the estimated monitor size to the image processing parameter determination unit 42.

Figure 12:
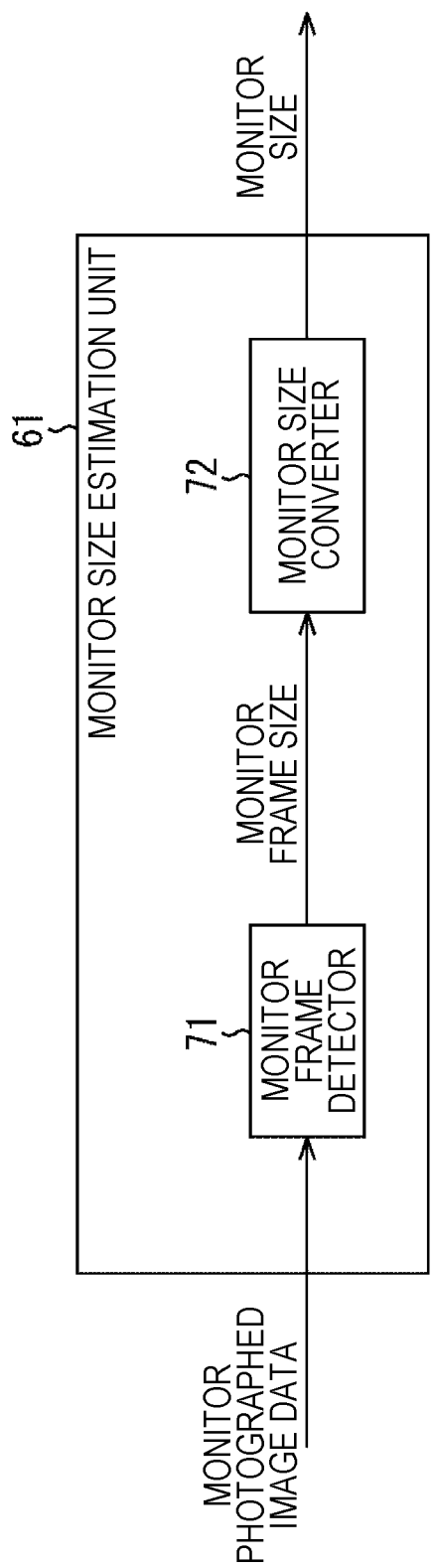
FIG. 12 is a block diagram illustrating a first configuration example of a monitor size estimation unit 61.

FIG. 12 is a block diagram illustrating a first configuration example of the monitor size estimation unit 61 in FIG. 11.

In FIG. 12, the monitor size estimation unit 61 includes a monitor frame detector 71 and a monitor size converter 72.

The monitor photographed image is supplied from the endoscope 21 to the monitor frame detector 71.

The monitor frame detector 71 detects a monitor frame as an outer peripheral portion of the monitor 37, captured in the monitor photographed image from the endoscope 21. Furthermore, the monitor frame detector 71 detects the size of the monitor frame, that is, for example, the number of horizontal and vertical pixels of the substantially rectangular monitor frame, or the like, of the monitor 37 captured in the monitor photographed image, as the number of pixels of the pixel on which the monitor 37 is captured, and supplies the size to the monitor size converter 72.

The monitor size converter 72 stores a monitor size table (not illustrated) associating the size of the monitor frame when the monitors of individual monitor sizes are photographed with the monitor sizes obtained at photographing at a predetermined distance apart from the monitor.

With reference to the monitor size table, the monitor size converter 72 converts the size of the monitor frame supplied from the monitor frame detector 71 into a monitor size corresponding to the size of the monitor frame, and outputs the monitor size as an estimation result of the monitor size of the monitor 37.

Figure 13:
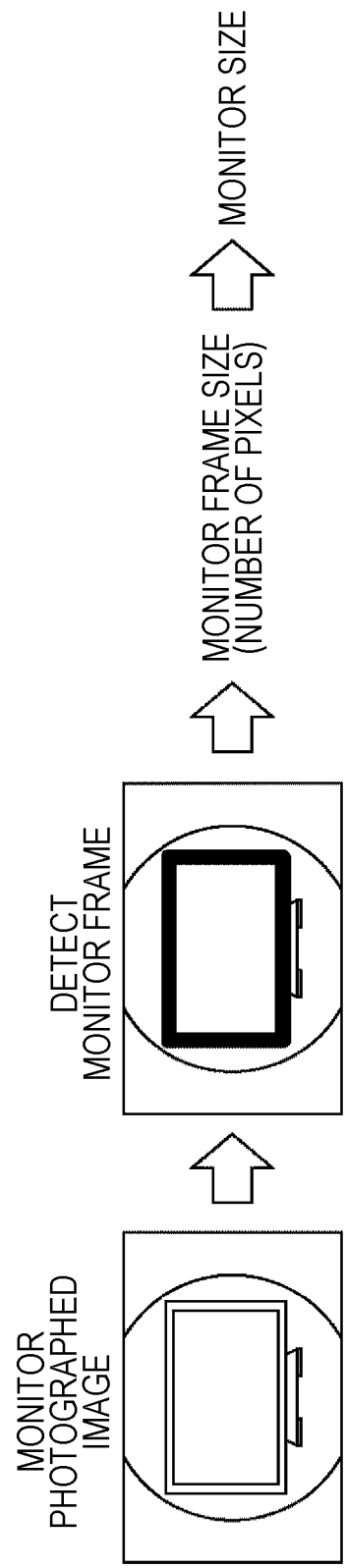
FIG. 13 is a diagram illustrating an example of processing of the monitor size estimation unit 61.

FIG. 13 is a diagram illustrating an example of processing of the monitor size estimation unit 61 in FIG. 12.

For example, before starting the surgery, the CCU 31 displays on the monitor 37 or the like a message prompting the endoscope 21 to photograph the monitor 37 at a position apart from the monitor 37 by a predetermined distance.

The user such as a practitioner photographs the monitor 37 by the endoscope 21 at a position apart from the monitor 37 by the predetermined distance in accordance with the message displayed on the monitor 37. The monitor photographed image obtained by photographing the monitor 37 with the endoscope 21 is supplied to the monitor size estimation unit 61.

The monitor frame detector 71 in the monitor size estimation unit 61 (FIG. 12) performs edge detection on the monitor photographed image from the endoscope 21, for example, so as to detect the monitor frame of the monitor 37 captured in the monitor photographed image.

Furthermore, the monitor frame detector 71 detects the number of pixels as the size of the monitor frame and supplies the detected result to the monitor size converter 72.

With reference to the monitor size table, the monitor size converter 72 converts the size of the monitor frame supplied from the monitor frame detector 71 into a monitor size and outputs the monitor size as the estimation result of the monitor size of the monitor 37.

In the first configuration example of the monitor size estimation unit 61 in FIG. 11, there is a need to prepare the monitor size table beforehand and to perform the photographing of the monitor 37 by the user from a position apart from the monitor 37 by a predetermined distance.

Figure 14:
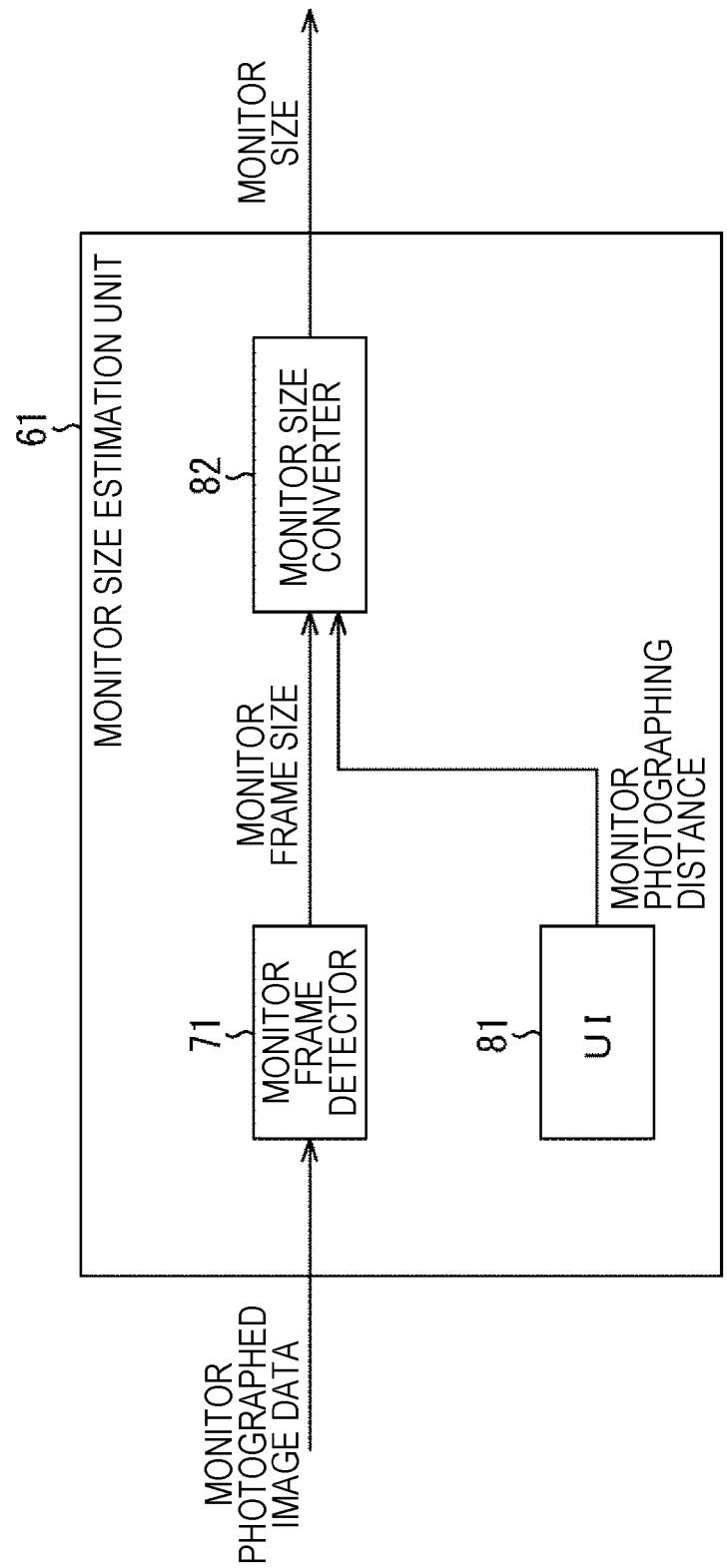
FIG. 14 is a block diagram illustrating a second configuration example of the monitor size estimation unit 61.

FIG. 14 is a block diagram illustrating a second configuration example of the monitor size estimation unit 61 in FIG. 11.

Note that in the figure, portions corresponding to the case of FIG. 12 are denoted by the same reference numerals, and the description thereof will be omitted as appropriate below.

In FIG. 14, the monitor size estimation unit 61 includes the monitor frame detector 71, a UI 81, and a monitor size converter 82.

Accordingly, the monitor size estimation unit 61 of FIG. 14 has a shared configuration with the case of FIG. 12 in that it includes the monitor frame detector 71.

Note that the monitor size estimation unit 61 in FIG. 14 differs from the case of FIG. 12 in that the monitor size converter 82 is provided in place of the monitor size converter 72, and that the UI 81 is newly provided.

The UI 81 is operated by a user such as a practitioner, for example. The user can input the monitor photographing distance when photographing the monitor 37 by operating the UI 81. The UI 81 supplies the monitor photographing distance input by the user's operation to the monitor size converter 82.

That is, FIG. 14 is a case similar to the case of FIG. 12, where the user such as the practitioner photographs the monitor 37 by the endoscope 21 before the start of surgery.

Note that while FIG. 12 illustrates a case where the user needs to photograph the monitor 37 at a position apart from the monitor 37 by a predetermined distance, FIG. 14 illustrates a case where the user can photograph the monitor 37 at an arbitrary position.

Also note that in the case of FIG. 14, the user operates the UI 81 to input the monitor photographing distance when photographing the monitor 37, that is, the distance from the user's position (more precisely, the position of the endoscope 21) when the user photographed the monitor 37 to the monitor 37.

The monitor size converter 82 stores a distance/monitor size table (not illustrated) associating the size of the monitor frame when the monitors of individual monitor sizes are photographed with the monitor sizes obtained at a position at each of a predetermined plurality of separation distances, for example.

With reference to the distance/monitor size table, the monitor size converter 82 converts the monitor photographing distance supplied from the UI 81 and the monitor frame size supplied from the monitor frame detector 71 into a monitor size corresponding to the monitor photographing distance and the monitor frame size, and outputs the monitor size as the estimation result of the monitor size of the monitor 37.

According to the monitor size estimation unit 61 in FIG. 14, while the user needs to input the monitor photographing distance by operating the UI 81, it is possible to photograph the monitor 37 at an arbitrary monitor photographing distance.

Figure 15:
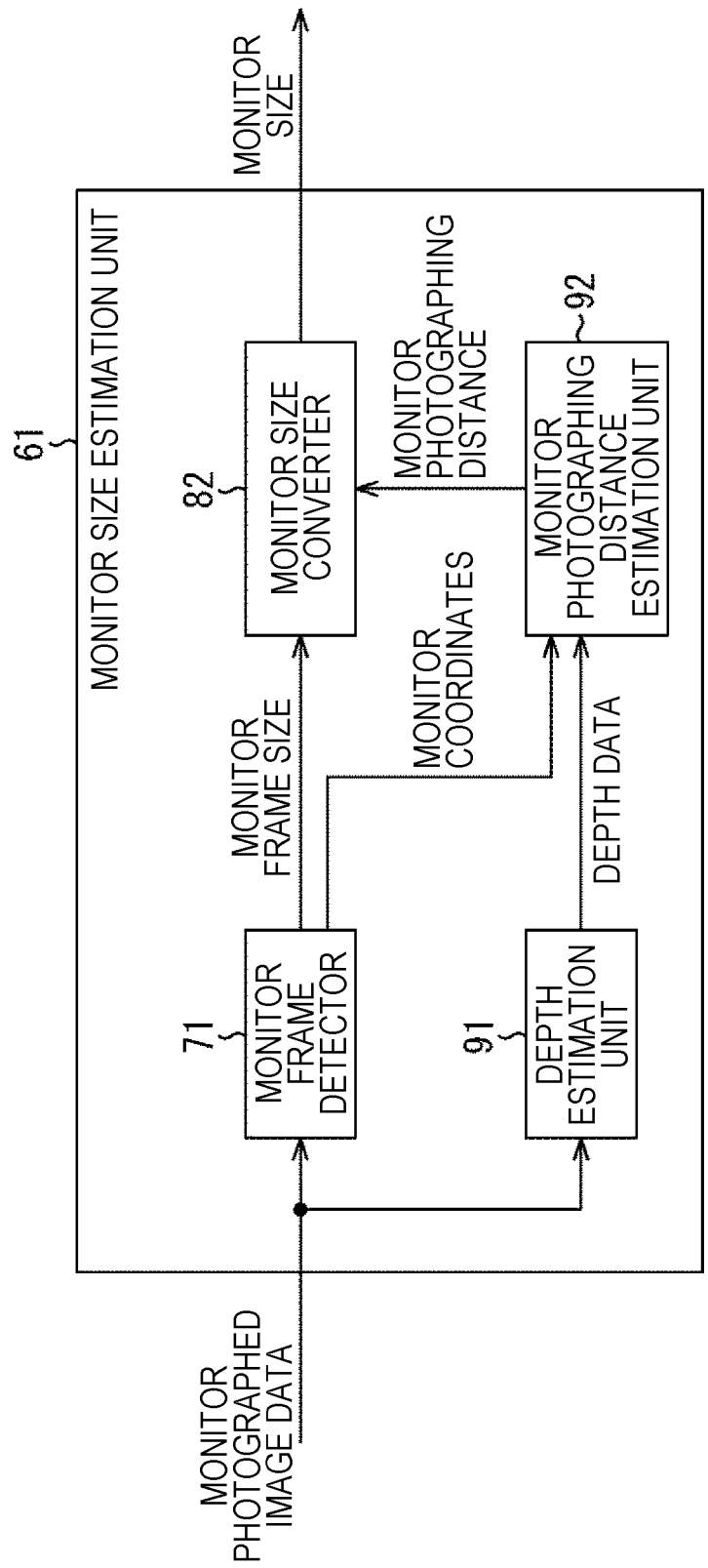
FIG. 15 is a block diagram illustrating a third configuration example of the monitor size estimation unit 61.

FIG. 15 is a block diagram illustrating a third configuration example of the monitor size estimation unit 61 in FIG. 11.

Note that in the figure, portions corresponding to the case of FIG. 14 are denoted by the same reference numerals, and the description thereof will be omitted as appropriate below.

In FIG. 15, the monitor size estimation unit 61 includes the monitor frame detector 71, the monitor size converter 82, a depth estimation unit 91, and a monitor photographing distance estimation unit 92.

Therefore, the monitor size estimation unit 61 of FIG. 15 is similar to the case of FIG. 14 in that it includes the monitor frame detector 71 and the monitor size converter 82.

Note that the monitor size estimation unit 61 in FIG. 15 differs from the case in FIG. 14 in that the depth estimation unit 91 and the monitor photographing distance estimation unit 92 are provided in place of the UI 81.

Herein, FIG. 15 is a case where the endoscope 21 includes a stereo camera as a multi-view camera, for example, and outputs a stereoscopic image of two viewpoints including a left (L) image and a right (R) image as a monitor photographed image.

The monitor photographed image as a stereoscopic image is supplied from the endoscope 21 to the depth estimation unit 91.

The depth estimation unit 91 uses one of the L image and the R image included in the stereoscopic image as a standard image while defining the other image as a reference image and detects a parallax of each of the pixels of the standard image with respect to the reference image.

Furthermore, the depth estimation unit 91 estimates (obtains) a depth (distance in the depth direction) of each of pixels of the standard image, that is, the depth of a subject captured on each of the pixels of the standard image, from the parallax of each of the pixels of the standard image, and supplies the obtained depth to the monitor photographing distance estimation unit 92.

Note that while in FIG. 15, the monitor frame detector 71 detects the size of the monitor frame from the stereoscopic image as the monitor photographed image from the endoscope 21, the detection of the monitor frame is performed on the standard image among the L image and the R image to form the stereoscopic image, as a target.

In addition, in FIG. 15, the monitor frame detector 71 detects the size of the monitor frame and also the coordinates of the monitor frame, that is, the coordinates of the pixels (entirely or partially) included in the monitor frame (and inside of the monitor frame) as monitor coordinates, and supplies the detected coordinates to the monitor photographing distance estimation unit 92.

From among the depths of individual pixels of the standard image from the depth estimation unit 91, the monitor photographing distance estimation unit 92 detects the depth of the pixel at the position of the monitor coordinates from the monitor frame detector 71, that is, the depth of the pixel on which the monitor frame (and inside of the monitor frame) is captured.

Furthermore, the monitor photographing distance estimation unit 92 estimates the monitor photographing distance from the depth of the pixel on which the monitor frame is captured, and supplies the estimated distance to the monitor size converter 82.

That is, for example, the monitor photographing distance estimation unit 92 obtains (estimates) the depth of an arbitrary one of the depths of the pixels included in the monitor frame, an average value, a mode value, a minimum value or a maximum value of the depths of the pixels included in the monitor frame or the like, as the monitor photographing distance, and supplies the obtained distance to the monitor size converter 82.

Similarly to the case of FIG. 14, with reference to the distance/monitor size table, the monitor size converter 82 converts the monitor photographing distance supplied from the monitor photographing distance estimation unit 92 and the monitor frame size supplied from the monitor frame detector 71 into a monitor size corresponding to the monitor photographing distance and the monitor frame size, and outputs the monitor size as the estimation result of the monitor size of the monitor 37.

With the monitor size estimation unit 61 in FIG. 15, the user can photograph the monitor 37 at an arbitrary monitor photographing distance without a need to input the monitor photographing distance.

Note that in FIG. 15, while the depth estimation unit 91 estimates the depths of all the pixels of the standard image, the depth estimation unit 91 may selectively obtain, for example, the depth of pixel on which the monitor frame (and inside of the monitor frame) is captured and the pixels in the vicinity of the pixel, among the pixels of the standard image.

That is, in FIG. 15, it is allowable to configure such that the monitor coordinates are supplied from the monitor frame detector 71 to the depth estimation unit 91 rather than the monitor photographing distance estimation unit 92, and the depth estimation unit 91 selectively obtains the depth of the pixels on which the monitor frame is captured or the pixel in the vicinity of the pixel among the pixels of the standard image, and then supplies the depth to the monitor photographing distance estimation unit 92.

In this case, the monitor photographing distance estimation unit 92 estimates the monitor photographing distance from the depth of the pixel on which the monitor frame is captured and the pixels in the vicinity of the pixel, which are supplied from the monitor frame detector 71.

Figure 16:
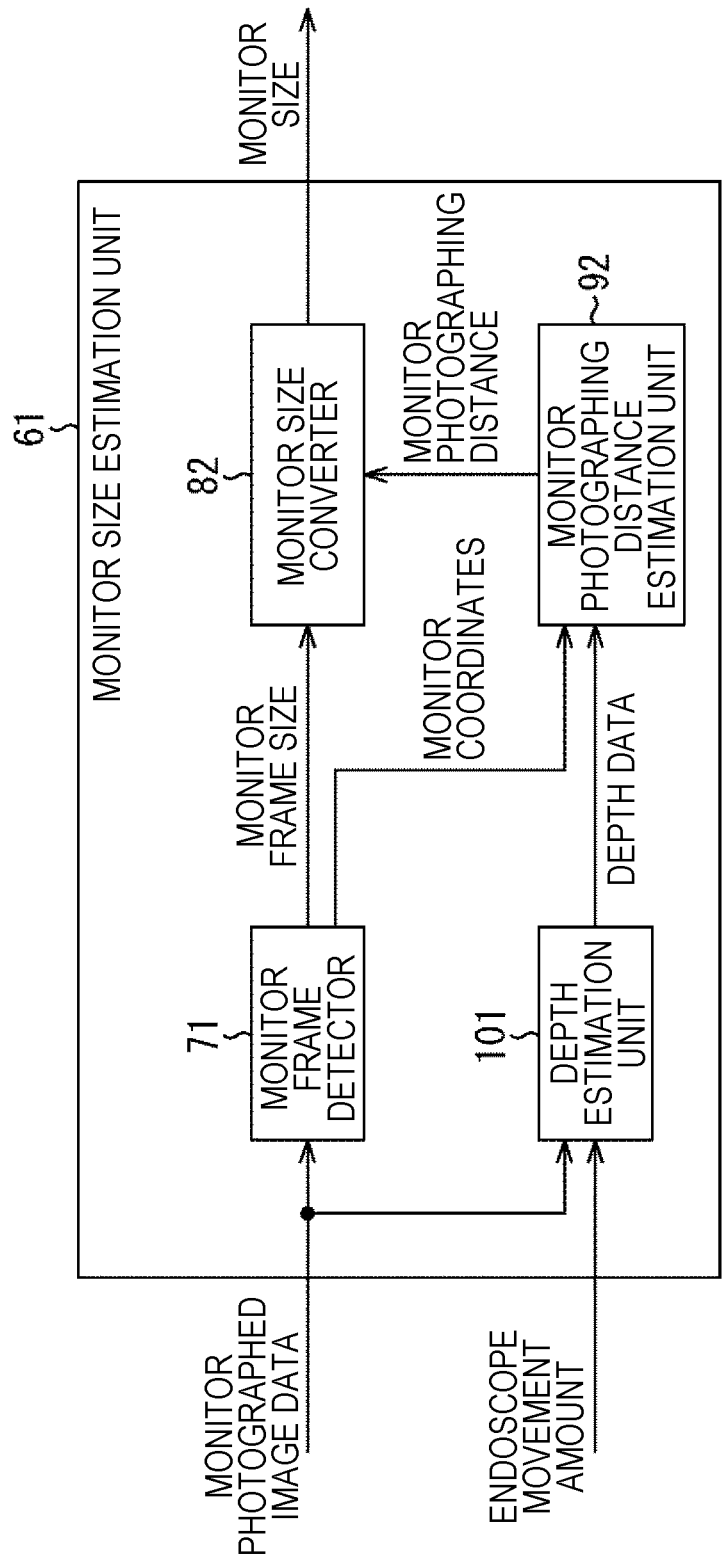
FIG. 16 is a block diagram illustrating a fourth configuration example of the monitor size estimation unit 61.

FIG. 16 is a block diagram illustrating a fourth configuration example of the monitor size estimation unit 61 in FIG. 11.

Note that in the figure, portions corresponding to the case of FIG. 15 are denoted by the same reference numerals, and the description thereof will be omitted as appropriate below.

In FIG. 16, the monitor size estimation unit 61 includes the monitor frame detector 71, the monitor size converter 82, the monitor photographing distance estimation unit 92, and a depth estimation unit 101.

Therefore, the monitor size estimation unit 61 of FIG. 16 is similar to the case of FIG. 15 in that it includes the monitor frame detector 71, the monitor size converter 82, and the monitor photographing distance estimation unit 92.

Note that the monitor size estimation unit 61 in FIG. 16 differs from the case of FIG. 15 in that the depth estimation unit 101 is provided in place of the depth estimation unit 91.

Note that while FIG. 15 described above is a case where the endoscope 21 has the stereo camera and outputs the stereoscopic image as the monitor photographed image, FIG. 16 is a case where the endoscope 21 has a single-view camera, and an image of one viewpoint is output as the monitor photographed image.

Note that FIG. 16 is a case where the endoscope 21 (a camera head or the like thereof) has a movement amount detection function of detecting the movement amount of the single-view camera of the endoscope 21 such as a gyro sensor, for example, and the movement amount of the single-view camera detected by the movement amount detection function is supplied to the depth estimation unit 101 as the endoscope movement amount.

As described above, while the endoscope movement amount is supplied from the endoscope 21 to the depth estimation unit 101, a single-view image as a monitor photographed image photographed by the single-view camera is also supplied from the endoscope 21 to the depth estimation unit 101.

Herein, FIG. 16 illustrates a configuration enabling the user to photograph the monitor 37 at an arbitrary monitor photographing distance as in the cases of FIGS. 14 and 15. Note that FIG. 16 is a case where the user is to photograph the monitor 37 at different timings from different photographing positions.

This photographing enables acquisition, as the monitor photographed image, of images of two viewpoints photographed at different timings from different photographing positions, that is, images corresponding to the L image and the R image to form the stereoscopic image.

The images of the two viewpoints as described above are supplied to the depth estimation unit 101 from the endoscope 21 as the monitor photographed image.

On the basis of the endoscope movement amount from the endoscope 21, the depth estimation unit 101 obtains the movement amount (vector) of the single-view camera of the endoscope 21 when the two-viewpoint image as the monitor photographed image from the endoscope 21 is photographed.

Furthermore, the depth estimation unit 101 defines one of the two-viewpoint images as the monitor photographed image from the endoscope 21 as a standard image while defining the other image as a reference image, and detects a parallax of each of the pixels of the standard image with respect to the reference image using the movement amount of the single-view camera.

Subsequently, the depth estimation unit 101 estimates a depth of each of pixels of the standard image (depth of the subject captured in each of pixels of the standard image) from the parallax of each of the pixels of the standard image, and supplies the estimated depth to the monitor photographing distance estimation unit 92.

Herein, detection of the monitor frame size and monitor coordinates in FIG. 16 by the monitor frame detector 71 is performed onto the standard image as in the case of FIG. 15.

Figure 17:
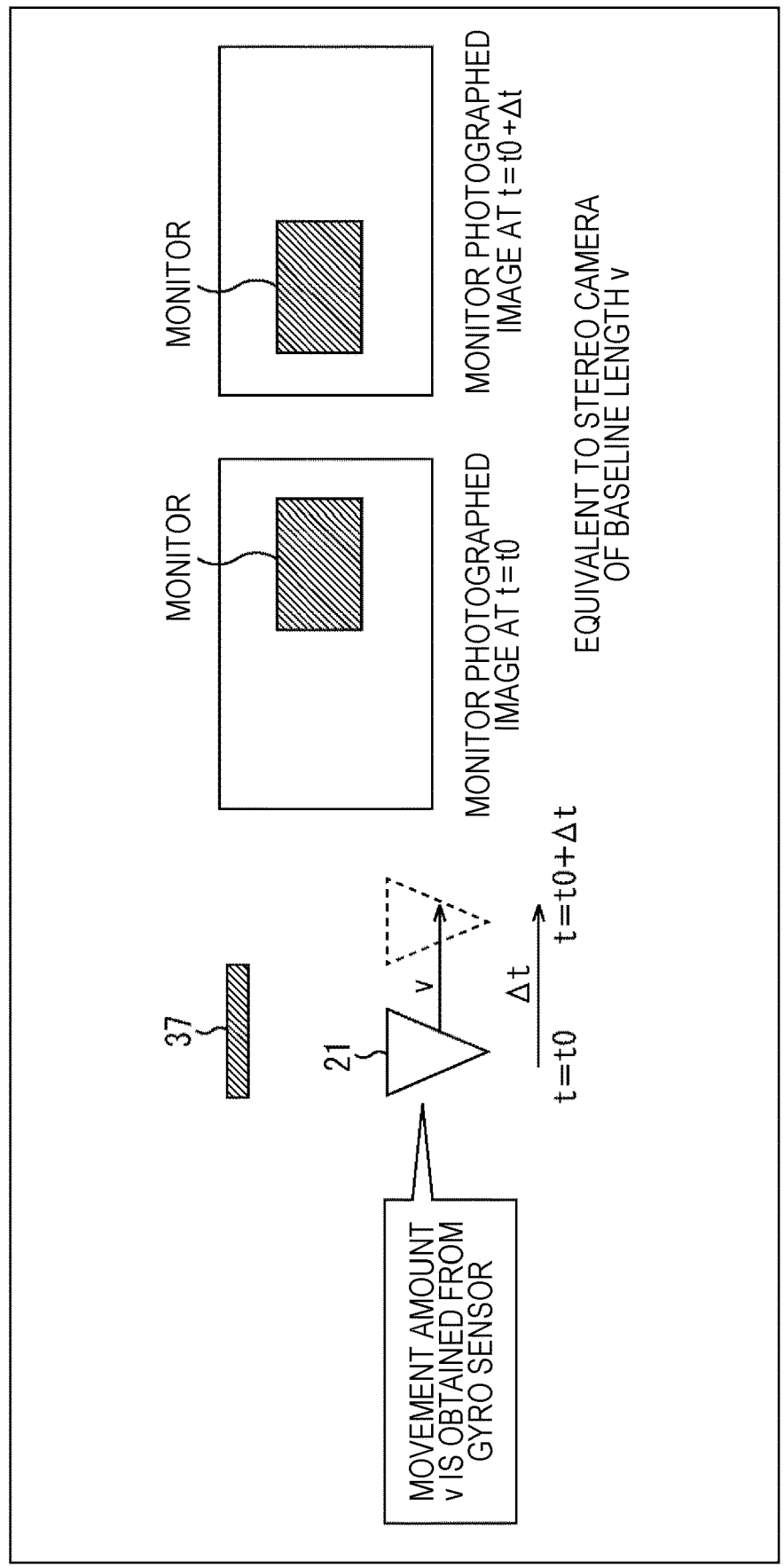
FIG. 17 is a diagram illustrating estimation of a depth of each of pixels of a standard image in a depth estimation unit 101.

FIG. 17 is a diagram illustrating estimation of a depth of each of pixels of a standard image in the depth estimation unit 101 of FIG. 16.

Now, it is assumed that a user photographs the monitor 37 by the endoscope 21 at time t=t0 and thereafter the user moves and photographs the monitor 37 by the endoscope 21 at time t=t0+Δt at a position different from the position of the time t=t0.

Now, in order to simplify the explanation, it is assumed that the user performs the photographing of the monitor 37 at the time t=t0 and the time t=t0+Δt while moving horizontally in a plane parallel to the display screen of the monitor 37, and that the movement amount of the single-view camera of the endoscope 21 at that time is v.

In this case, the monitor photographed image being the image of one viewpoint photographed at the time t=t0 and the monitor photographed image being the image of one viewpoint photographed at the time t=t0+Δt are to be an image equivalent to a stereo image (L image and R image to form the stereoscopic image) photographed by a stereo camera in which a baseline length (distance between optical centers of two cameras forming the stereo camera) is the movement amount v.

Therefore, the depth estimation unit 101 can detect the parallax and eventually the depth similarly to the depth estimation unit 91 in FIG. 15 by using the movement amount v.

With the monitor size estimation unit 61 of FIG. 16, it is also possible to estimate the monitor size of the monitor 37 without user's input of monitor photographing distance even in a case where the endoscope 21 has a single-view camera rather than a multi-view camera such as a stereo camera.

Note that, the depth (and eventually the monitor photographing distance) of the subject captured in the pixels of the monitor photographed image can be detected (estimated) using, for example, focus information of the endoscope 21, for example, as a camera for photographing the monitor 37.

Furthermore, the depth of the subject captured in the pixels of the monitor photographed image can be detected using a distance sensor such as a time of flight (ToF) sensor, for example. For example, according to the ToF sensor, light is emitted from a light emitting element, and the reflected light reflected from the subject is received by a light receiving element. Then, the distance to the subject can be obtained in accordance with the time from emission of the light from the light emitting element to reception of the reflected light at the light receiving element.

Note that in estimation of the monitor size by the monitor size estimation unit 61, the detection of the monitor 37 captured in the monitor photographed image can be performed by edge detection targeting the monitor photographed image, or by the depth of the subject captured in the pixels of the monitor photographed image together with the edge detection.

Moreover, the detection of the monitor 37 captured in the monitor photographed image can be performed by previously registering color information representing the color of the monitor frame and by using the color information and the edge detection targeted for the monitor photographed image.

Furthermore, in order to handle the case where the monitor 37 is photographed from a diagonal direction, it is possible to estimate an angle (photographing angle when the monitor 37 is photographed) on the basis of a width of a peak region of an integrated value of edge detection (for example, the integrated value such as a primary differential value or a secondary differential value obtained by edge detection) and it is possible to estimate the monitor size in consideration of a photographing angle.

In addition, it is possible in the endoscopic surgical system to register beforehand the monitor and monitor size applied in individual surgeries. In this case, the monitor size can be obtained from the monitor size registered beforehand without performing estimation (detection).

<Fourth Configuration Example of CCU 31>

Figure 18:
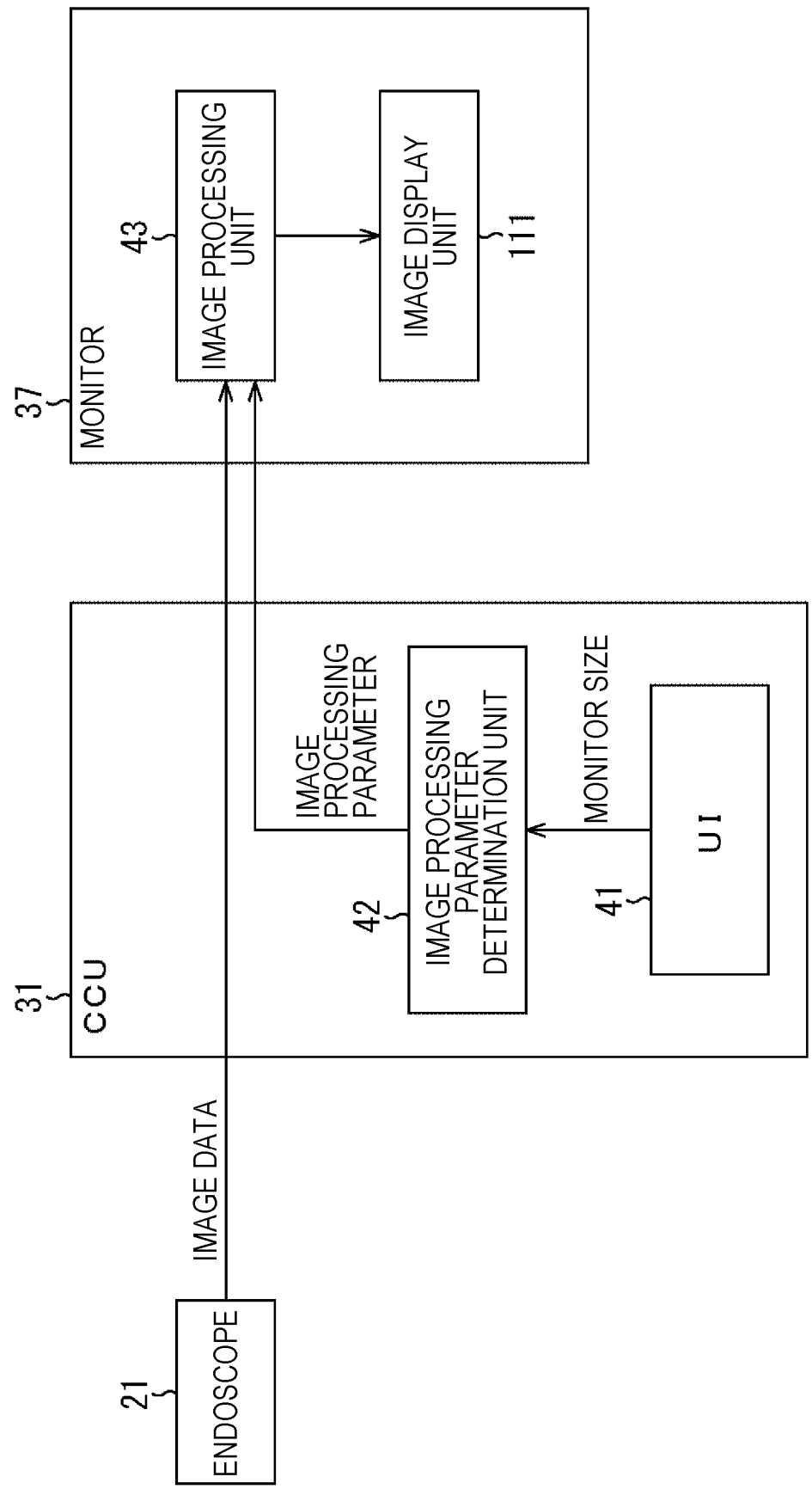
FIG. 18 is a block diagram illustrating a fourth configuration example of the CCU 31.

FIG. 18 is a block diagram illustrating a fourth configuration example of the CCU 31 in FIG. 1.

Note that in the figure, portions corresponding to the case of FIG. 2 are denoted by the same reference numerals, and the description thereof will be omitted as appropriate below.

In FIG. 18, the CCU 31 includes the UI 41 and the image processing parameter determination unit 42.

Accordingly, the CCU 31 of FIG. 18 has a configuration similar to the case of FIG. 2 in that it includes the UI 41 and the image processing parameter determination unit 42 and differs from the case of the FIG. 2 in that the image processing unit 43 is not provided.

Instead, the monitor 37 includes the image processing unit 43 and an image display unit 111 in FIG. 18.

An image processed surgical site image is supplied from the image processing unit 43 to the image display unit 111.

The image display unit 111 is a block that controls original display functions of the monitor 37 and displays a surgical site image supplied from the image processing unit 43.

With the above-configured CCU 31, the surgical site image supplied from the endoscope 21 is supplied to the image processing unit 43 of the monitor 37.

Furthermore, the image processing parameters determined by the image processing parameter determination unit 42, in the CCU 31, are supplied to the image processing unit 43 of the monitor 37.

In the monitor 37, similarly to the case of FIG. 2, the image processing unit 43 performs image processing on the surgical site image supplied from the endoscope 21 via the CCU 31 using the image processing parameter from the image processing parameter determination unit 43, so as to perform image processing corresponding to the monitor size of the monitor 37 on the surgical site image. Then, the image processing unit 43 supplies the surgical site image that has undergone the image processing to the image display unit 111 so as to display the image.

As described above, the image processing unit 43 can be provided on the monitor 37 rather than the CCU 31.

Note that the image processing unit 43 can be provided in any of the CCU 31 and the monitor 37, or both of the CCU 31 and the monitor 37. This case makes it possible to configure such that the CCU 31 performs a portion of image processing such as NR processing, for example, and that the monitor 37 performs the remaining image processing such as enhancement processing, for example.

Moreover, FIG. 18 has a configuration of the CCU 31 in which the image processing parameter determination unit 42 determines, from the plurality of image processing parameters stored in the parameter storage unit 52 (FIG. 3), the image processing parameter to be used for image processing by the image processing unit 43 (target parameter) in accordance with the monitor size of the monitor 37, and supplies the determined parameter to the image processing unit 43 of the monitor 37. In addition, the CCU 31 is also capable of supplying the plurality of image processing parameters (table including the parameters) stored in the parameter storage unit 52 (FIG. 3) of the image processing parameter determination unit 42 to the monitor 37.

Since the monitor 37 has information of its own monitor size, the monitor 37 can determine an image processing parameter corresponding to the monitor size of the monitor 37 from among the plurality of image processing parameters supplied from the CCU 31 (stored in the parameter storage unit 52).

Accordingly, this case makes it possible to have a configuration of the CCU 31 without the UI 41 used for inputting the monitor size by the user.

Furthermore, while the CCU 31 in FIG. 18 includes the UI 41 for inputting the monitor size by the user, the monitor size can be transmitted from the monitor 37 to the CCU 31 as described with reference to FIG. 10 for example or can be estimated from the monitor photographed image of the monitor 37 as described with reference to FIG. 11.

Furthermore, FIG. 18 can be configured such that the image processing parameter determination unit 42 is provided in the monitor 37 rather than the CCU 31.

<Fifth Configuration Example of CCU 31>

Figure 19:
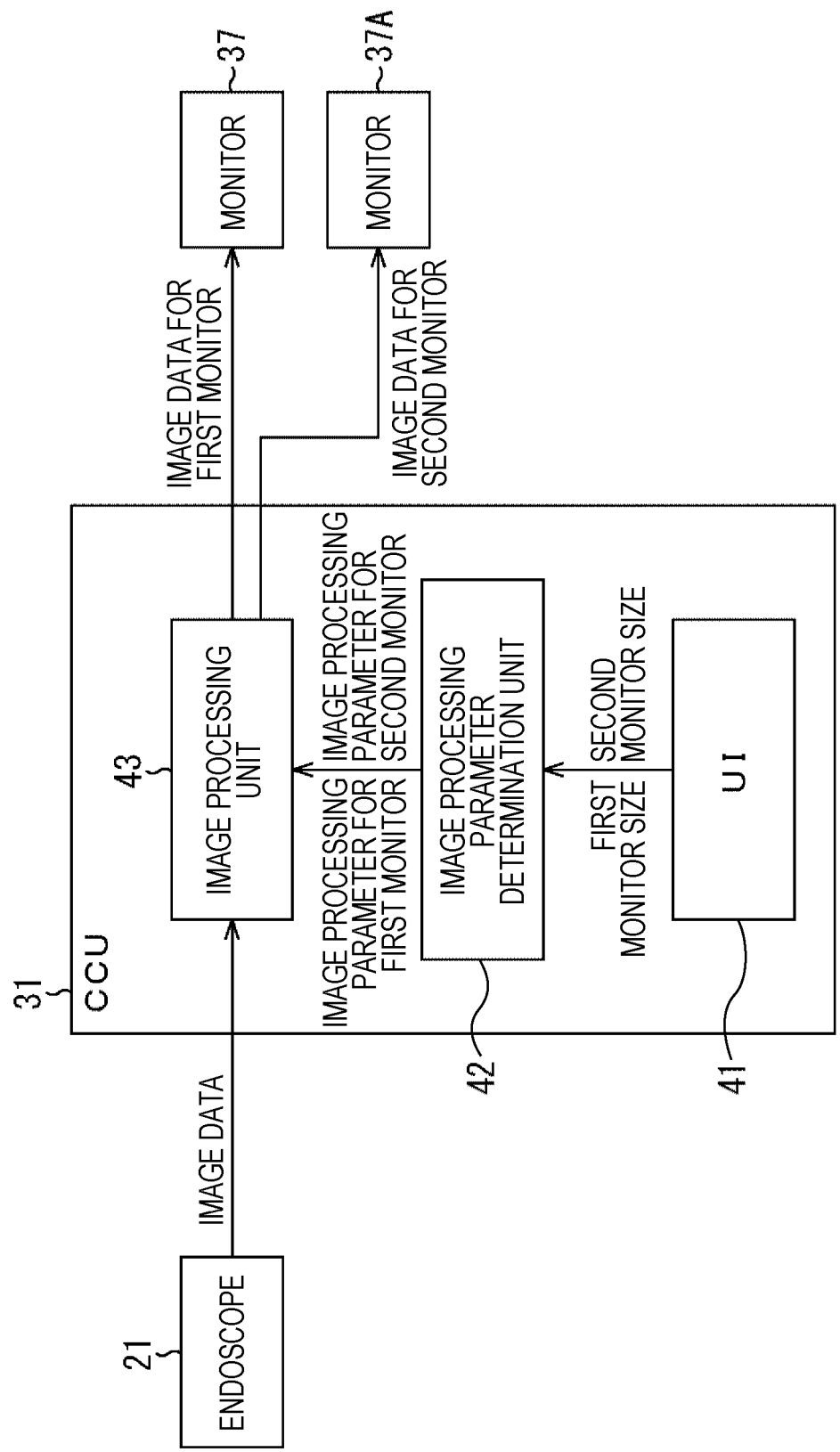
FIG. 19 is a block diagram illustrating a fifth configuration example of the CCU 31.

FIG. 19 is a block diagram illustrating a fifth configuration example of the CCU 31 in FIG. 1.

Note that in the figure, portions corresponding to the case of FIG. 2 are denoted by the same reference numerals, and the description thereof will be omitted as appropriate below.

In FIG. 19, the CCU 31 includes the UI 41, the image processing parameter determination unit 42, and the image processing unit 43.

Therefore, the CCU 31 of FIG. 19 is configured similarly to the case of FIG. 2.

Note that in the case of FIG. 19, for example, two monitors 37 and 37A as a plurality of monitors are connected to the CCU 31.

With this configuration, the user operates the UI 41 to input monitor sizes of the monitor 37 as a first monitor and the monitor 37A as a second monitor, and then, the UI 41 supplies the monitor size of the monitor 37 (hereinafter also referred to as a first monitor size) and the monitor size of the monitor 37A (hereinafter also referred to as a second monitor size) that have been input by user's operation, to the image processing parameter determination unit 42.

The image processing parameter determination unit 42 obtains the first monitor size and the second monitor size from the UI 41.

Then, the image processing parameter determination unit 42 determines an image processing parameter (hereinafter, also referred to as an image processing parameter for the first monitor) to be used for image processing in the image processing unit 43 in accordance with the first monitor size from the UI 41, and supplies the determined parameter to the image processing unit 43.

Furthermore, the image processing parameter determination unit 42 determines an image processing parameter (hereinafter, also referred to as an image processing parameter for the second monitor) to be used for image processing in the image processing unit 43 in accordance with the second monitor size from the UI 41, and supplies the determined parameter to the image processing unit 43.

The image processing unit 43 uses the image processing parameters for the first monitor from the image processing parameter determination unit 43 to perform image processing on a surgical site image from the endoscope 21 so as to perform image processing on a surgical site image corresponding to the first monitor size of the monitor 37 that displays the surgical site image that has undergone the image processing. Then, the image processing unit 43 outputs the surgical site image that has undergone the image processing performed using the image processing parameter for the first monitor as an image (or image data) for the first monitor. This image for the first monitor is supplied to and displayed on the monitor 37 as the first monitor.

Moreover, the image processing unit 43 uses the image processing parameters for the second monitor from the image processing parameter determination unit 43 to perform image processing on a surgical site image from the endoscope 21 so as to perform image processing on a surgical site image corresponding to the second monitor size of the monitor 37A that displays the surgical site image that has undergone the image processing. Then, the image processing unit 43 outputs the surgical site image after the image processing performed using the image processing parameter for the second monitor as an image (or image data) for the second monitor. This image for the second monitor is supplied to and displayed on the monitor 37A as the second monitor.

Accordingly, with the CCU 31 of FIG. 19, the monitor 37 as the first monitor displays a surgical site image having image quality appropriate for the first monitor size of the monitor 37. Furthermore, the monitor 37A as the second monitor displays a surgical site image having image quality appropriate for the second monitor size of the monitor 37A.

As a result, in a case where the surgical site images are displayed on each of the plurality of monitors, such as the two monitors 37 and 37A, it is possible to alleviate accumulation of fatigue caused by viewing a surgical site image to about the same extent in the user viewing the surgical site image displayed on the monitor 37 and the user viewing the surgical site image displayed on the monitor 37A.

Note that, while FIG. 19 is an exemplary case where the two monitors 37 and 37A are connected to the CCU 31, three or more monitors can be connected to the CCU 31.

Moreover, while FIG. 19 is an exemplary case where the same surgical site images (having same content) are displayed on the two monitors 37 and 37A, it is possible to display different surgical site images on the two monitors 37 and 37A. Specifically, it is possible to display a surgical site image photographed by the endoscope 21 on one of the two monitors 37 and 37A, for example, and to display a surgical site image photographed by another endoscope (not illustrated) on the other monitor.

Furthermore, other than the case of FIG. 19 in which the image processing unit 43 is provided in the CCU 31, it is possible to provide it in each of the monitors 37 and 37A, or in the CCU 31 together with the monitors 37 and 37A, as in the case described with FIG. 18.

Furthermore, while the CCU 31 in FIG. 19 includes the UI 41 for inputting the monitor size by the user, the monitor size can be transmitted from the monitor 37 to the CCU 31 as described with reference to FIG. 10 for example or can be estimated from the monitor photographed image of the monitor 37 as described with reference to FIG. 11.

<Sixth Configuration Example of CCU 31>

Figure 20:
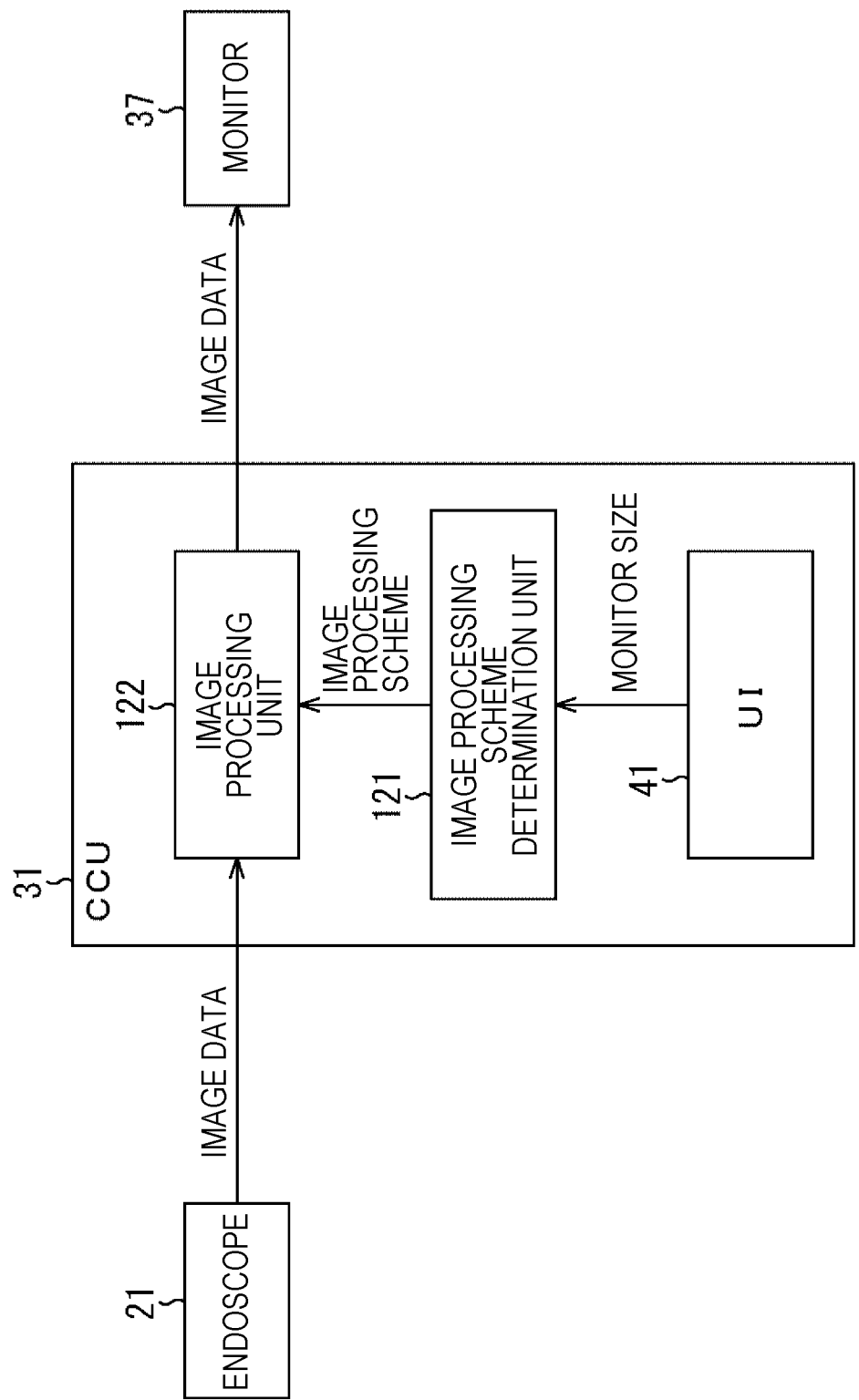
FIG. 20 is a block diagram illustrating a sixth configuration example of the CCU 31.

FIG. 20 is a block diagram illustrating a sixth configuration example of the CCU 31 in FIG. 1.

Note that in the figure, portions corresponding to the case of FIG. 2 are denoted by the same reference numerals, and the description thereof will be omitted as appropriate below.

In FIG. 20, the CCU 31 includes the UI 41, an image processing scheme determination unit 121, and an image processing unit 122.

Accordingly, the CCU 31 of FIG. 20 has a configuration similar to the case of FIG. 2 in that it includes the UI 41 and differs from the case of FIG. 2 in that the image processing scheme determination unit 121 and the image processing unit 122 are provided in place of the image processing parameter determination unit 42 and the image processing unit 43.

The image processing scheme determination unit 121 obtains the monitor size from the UI 41. The image processing scheme determination unit 121 determines an image processing scheme to be used for image processing by the image processing unit 122 in accordance with the monitor size from the UI 41 and supplies the determined image processing scheme to the image processing unit 122.

The image processing unit 122 uses the image processing scheme from the image processing scheme determination unit 121 to perform image processing on a surgical site image from the endoscope 21 so as to perform image processing on the surgical site image corresponding to the monitor size of the monitor 37 that displays the surgical site image that has undergone the image processing. Then, the image processing unit 122 supplies the surgical site image that has undergone the image processing to the monitor 37 so as to display the image.

As described above, image processing according to the monitor size of the monitor 37 can be performed also by image processing by an image processing scheme according to the monitor size as well as by image processing with an image processing parameter according to the monitor size.

That is, the intensity of the image processing performed on the surgical site image can be adjusted by changing the image processing scheme, as well as by adjusting the image processing parameter without changing the image processing scheme.

As described above, it is possible to provide a surgical site image having image quality appropriate for the monitor size of the monitor 37 also in the case of adjusting the intensity of the image processing performed on the surgical site image by changing the image processing scheme, similarly to the case of performing adjustment by changing the image processing parameters.

As described with reference to FIG. 9, examples of the correction processing as image processing performed on the surgical site image include NR processing, edge enhancement processing, contrast adjustment processing, parallax adjustment processing, and the like.

Examples of the (image) processing scheme of the NR processing include a processing scheme using a bilateral filter, a processing scheme using a Gaussian filter, a processing scheme using a median filter, and the like.

Example of the processing scheme of the edge enhancement processing include an unsharp mask and the like.

Examples of the processing scheme of the contrast adjustment processing include a processing scheme using tone curve correction, a processing scheme using histogram smoothing, and the like.

In adjusting the intensity of the correction processing by changing the (image) processing scheme of the correction processing as the image processing performed on the surgical site image in accordance with the monitor size, the processing scheme of the correction processing can be changed as follows.

Specifically, the NR processing scheme can be changed such that the larger the monitor size, the higher the intensity of the NR processing; and that the smaller the monitor size, the lower the intensity of the NR processing.

The edge enhancement processing scheme can be changed such that the larger the monitor size, the lower the intensity of the edge enhancement processing; and that the smaller the monitor size, the higher the intensity of the edge enhancement processing.

The contrast adjustment processing scheme can be changed such that the larger the monitor size, the lower the intensity of the contrast adjustment processing; and that the smaller the monitor size, the higher the intensity of the contrast adjustment processing.

The parallax adjustment processing scheme can be changed such that the larger the monitor size, the lower the intensity of the parallax adjustment processing; and that the smaller the monitor size, the higher the intensity of the parallax adjustment processing.

Note that, while FIG. 20 illustrates a case where one monitor 37 is connected to the CCU 31, a plurality of monitors can be connected to the CCU 31 as in the case of FIG. 19.

Furthermore, other than the case of FIG. 20 in which the image processing unit 122 is provided in the CCU 31, it is possible to provide it in the monitor 37, or both in the CCU 31 and in the monitors 37, as in the case described with FIG. 18.

Furthermore, while the CCU 31 in FIG. 20 includes the UI 41 for inputting the monitor size by the user, the monitor size can be transmitted from the monitor 37 to the CCU 31 as described with reference to FIG. 10 for example or can be estimated from the monitor photographed image of the monitor 37 as described with reference to FIG. 11.

Figure 21:
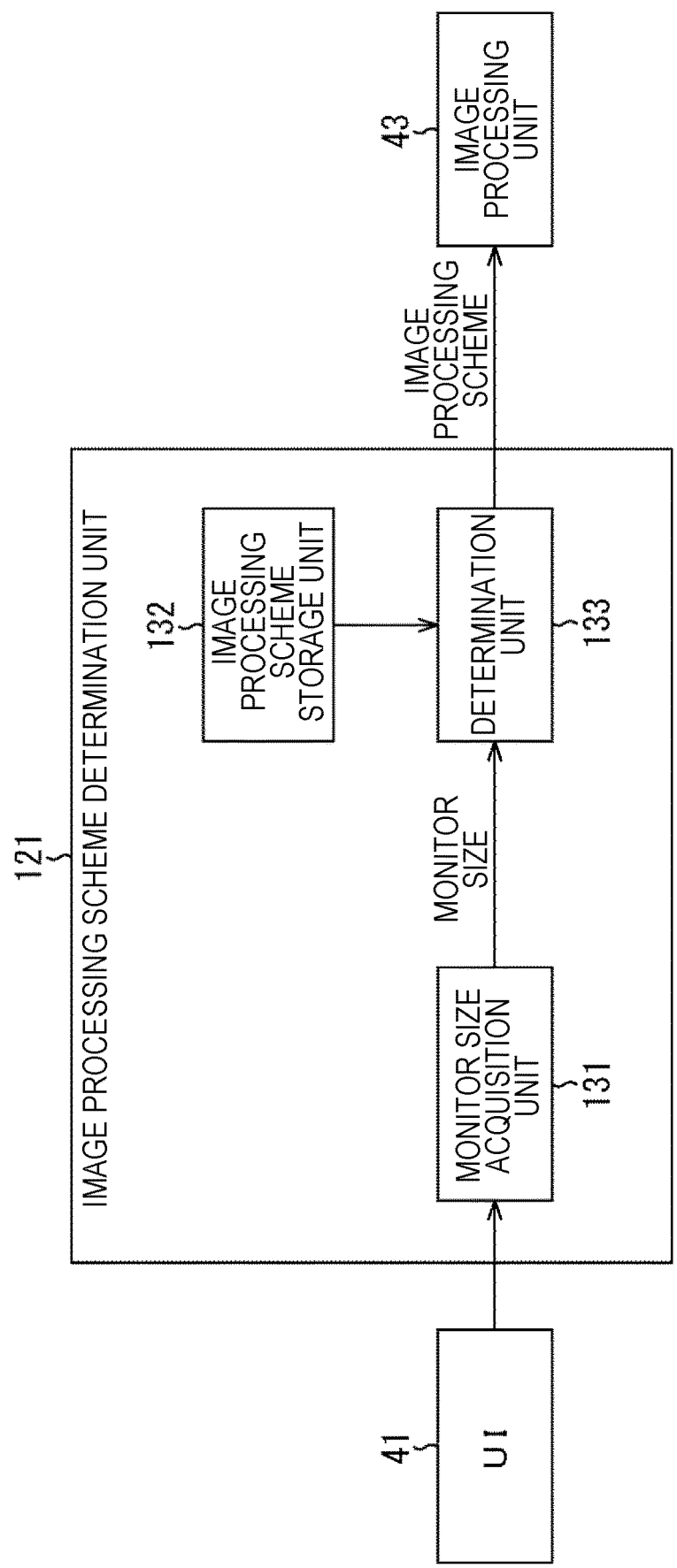
FIG. 21 is a block diagram illustrating a configuration example of an image processing scheme determination unit 121.

FIG. 21 is a block diagram illustrating a configuration example of an image processing scheme determination unit 121 in FIG. 20.

In FIG. 21, the image processing parameter determination unit 121 includes a monitor size acquisition unit 131, an image processing scheme storage unit 132, and a determination unit 133.

The monitor size acquisition unit 131 obtains the monitor size supplied from the UI 41 in FIG. 20 and supplies it to the determination unit 133, for example.

The image processing scheme storage unit 132 stores correction processing (processing information) appropriate for display of a surgical site image on each of monitors in association with information related to display of various monitors such as the monitor 37 displaying the surgical site image.

That is, the image processing scheme storage unit 132 stores each of a plurality of image processing schemes (information representing image processing schemes) of image processing (correction processing) that can be performed by the image processing unit 122 in FIG. 20, in association with each of a plurality of monitor sizes (information related to monitor display).

That is, the image processing scheme storage unit 132 stores the monitor size and the image processing scheme in which image processing of an intensity appropriate for the monitor size is performed in association with each other for each of the plurality of monitor sizes.

The determination unit 133 determines image processing schemes to be used for image processing by the image processing unit 122 from among a plurality of image processing schemes stored in the image processing scheme storage unit 132 in accordance with the monitor size supplied from the monitor size acquisition unit 131, and supplies the determined scheme to the image processing unit 122.

<Description of Computer Utilizing Present Technology>

Next, a series of processes performed on the units such as the image processing parameter determination unit 42, the image processing unit 43, the monitor size estimation unit 61, the image processing scheme determination unit 121, the image processing unit 122 can be implemented either by hardware or software. In a case where the series of processes is executed with software, a program included in the software is installed in a general-purpose computer, or the like.

Figure 22:
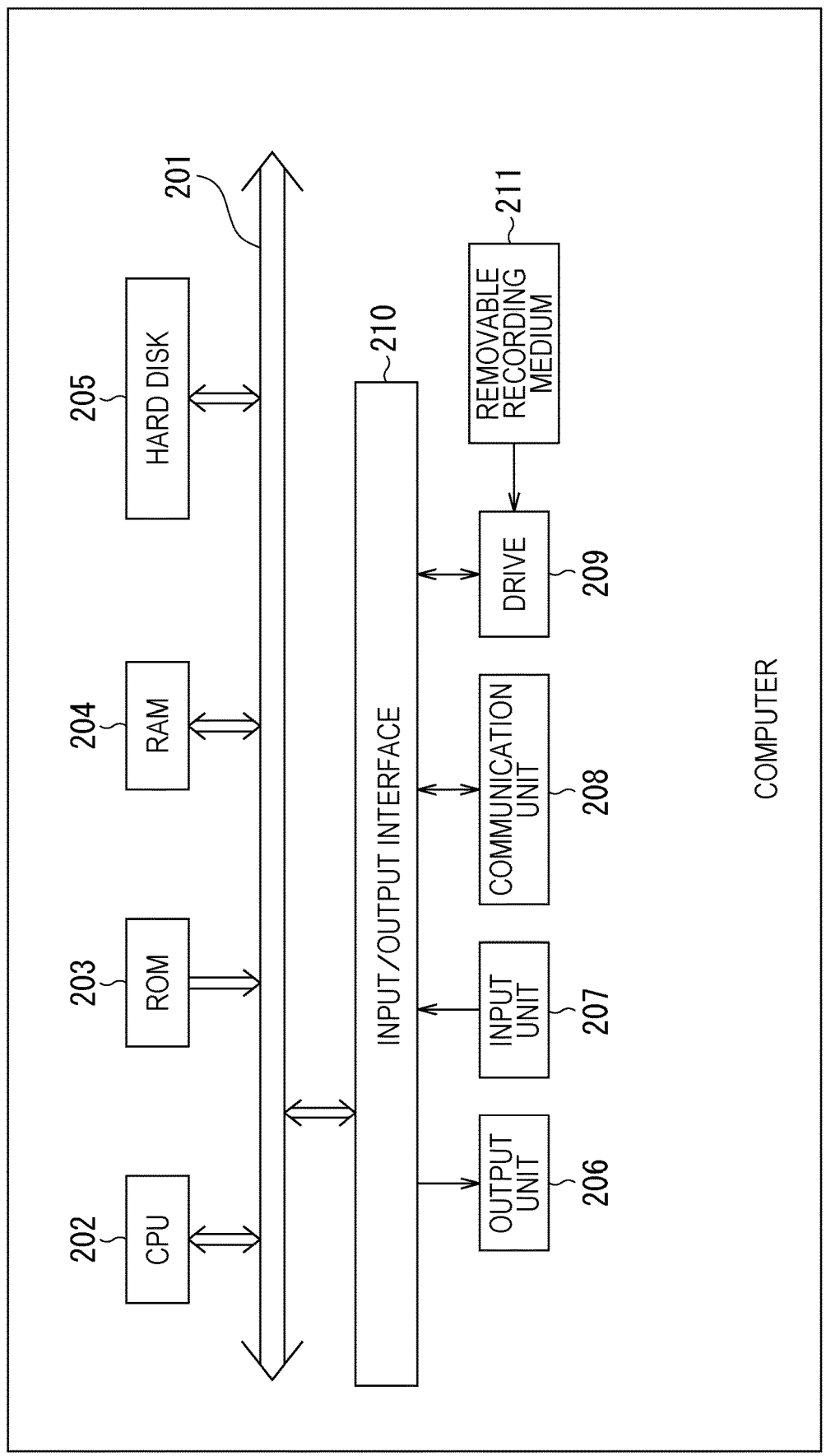
FIG. 22 is a block diagram illustrating an exemplary configuration of a computer according to an embodiment of the present technology.

Accordingly, FIG. 22 is a block diagram illustrating an exemplary configuration of a computer according to an embodiment, in which a program configured to execute the above-described series of processes is installed.

The program can be previously recorded in a hard disk 205 or a ROM 203, as a recording medium built into the computer.

Alternatively, the program can be stored (recorded) in a removable recording medium 211. The removable recording medium 211 can be supplied as package software. Examples of the removable recording medium 211 include a flexible disk, a compact disc read only memory (CD-ROM), a magneto optical (MO) disk, a digital versatile disc (DVD), a magnetic disk, a semiconductor memory, and the like.

Note that the program can be installed from the above-described removable recording medium 211 to the computer. Alternatively, the program can be downloaded to the computer via a communication network or a broadcasting network, and can be installed onto the built-in hard disk 205. Specifically, the program can be transferred, for example, from a downloading site to the computer wirelessly via an artificial satellite for digital satellite broadcasting, or can be transferred by wire to the computer via a network such as a local area network (LAN) and the Internet.

The computer incorporates a central processing unit (CPU) 202. The CPU 202 is connected to an input/output interface 210 via a bus 201.

When an instruction is input into the CPU 202 by operation, or the like, by a user, on an input unit 207 via the input/output interface 210, the CPU 202 executes a program stored in the read only memory (ROM) 203 according to the instruction. Alternatively, the CPU 202 loads the program stored in the hard disk 205 to a random access memory (RAM) 204 and executes the program.

With this procedure, the CPU 202 executes processing according to the above-described flowchart or processing done by the above-described configuration in the block diagram. Subsequently, the CPU 202 permits a processing result, as required, for example, to be output from an output unit 206, transmitted from a communication unit 208, recorded in the hard disk 205, via the input/output interface 210.

Note that the input unit 207 includes a keyboard, a mouse, a microphone, and the like. In addition, the output unit 206 includes a liquid crystal display (LCD), a speaker, and the like.

In this description, processing executed by a computer in accordance with a program need not be performed in time series along the order described in the flowchart. That is, processing executed by the computer according to the program includes processing executed in parallel or separately (e.g. parallel processing, or object processing).

In addition, the program can be processed by one computer (processor) or can be processed with distributed processing by a plurality of computers. Furthermore, the program can be transferred to a remote computer and be executed.

Furthermore, in the present description, the system represents a set of multiple constituents (devices, modules (parts), or the like). In other words, all the constituents may be in a same housing but they do not have to be in the same housing. Accordingly, a plurality of apparatuses, housed in separate housings, connected via a network can be a system. An apparatus in which a plurality of modules is housed in one housing can also be a system.

Note that embodiments of the present technology are not limited to the above-described embodiments but can be modified in a variety of ways within a scope of the present technology.

For example, the present technology can be applied to an endoscopic surgical system that performs endoscopic surgery as illustrated in FIG. 1, and in addition to this, can be applied to an electron microscope (medical microscope), any other apparatus displaying a surgical site image, and furthermore, applied to any other apparatus displaying an arbitrary image, for example.

Furthermore, the intensity of the image processing performed on the surgical site image can be adjusted by changing both the image processing parameter and the image processing scheme.

In addition, effects described herein are provided for purposes of exemplary illustration and are not intended to be limiting. Still other effects may also be contemplated.

Note that the present technology can be configured as follows.

<1>

An image processing apparatus including a control unit configured to control to perform correction processing on a surgical site image as a captured surgical site on the basis of information related to display of a display apparatus that displays the surgical site image.

<2>

The image processing apparatus according to <1>, in which the information related to the display includes display screen size, display resolution, and brightness of the display apparatus.

<3>

The image processing apparatus according to <1> or <2>, in which the control unit controls to perform correction processing on the surgical site image on the basis of the information related to the display and usage conditions of the display apparatus.

<4>

The image processing apparatus according to <3>, in which the usage conditions include brightness of a display apparatus installation location, a viewing distance and a viewing time of a viewer of the display apparatus.

<5>

The image processing apparatus according to any of <1> to <4>, in which the control unit controls the intensity of the correction processing on the basis of the information related to the display.

<6>

The image processing apparatus according to any of <1> to <5>, in which the correction processing includes noise removal processing, edge enhancement processing, contrast adjustment processing, and parallax adjustment processing.

<7>

The image processing apparatus according to any of <1> to <6>, in which the control unit controls a processing scheme of the correction processing on the basis of the information related to the display.

<8>

The image processing apparatus according to any of <1> to <6> further including a storage unit that stores correction processing appropriate for the display in association with the information related to the display, in which the control unit controls to perform the correction processing on the surgical site image on the basis of the correction processing stored in the storage unit.

<9>

The image processing apparatus according to any of <1> to <8> in which the control unit further controls to obtain the information related to the display.

<10>

The image processing apparatus according to <9>, in which the control unit obtains the information related to the display from the display apparatus.

<11>

The image processing apparatus according to <2>, in which the control unit estimates the display screen size from a photographed image obtained by photographing a display screen of the display apparatus, and controls to perform the correction processing on the surgical site image on the basis of the display screen size.

<12>

The image processing apparatus according to <11>, in which the control unit estimates the display screen size on the basis of the photographed image and a photographing distance when the photographed image is photographed.

<13>

The image processing apparatus according to <12>, in which the photographed image is an image of at least two viewpoints photographed by a multi-view camera, and the control unit estimates the photographing distance from the image of the two viewpoints.

<14>

The image processing apparatus according to <12>, in which the control unit estimates the photographing distance from focus information of the photographed image.

<15>

The image processing apparatus according to any of <1> to <14>, in which the control unit controls to perform the correction processing on the basis of the information related to the display of each of a plurality of display apparatuses in a case where the surgical site image is to be displayed on the plurality of display apparatuses.

<16>

The image processing apparatus according to any of <1> to <15>, in which the control unit further controls to display a corrected surgical site image that has undergone the correction processing, on the display apparatus.

<17>

An image processing method including controlling to perform correction processing on a surgical site image as a captured surgical site on the basis of information related to display of a display apparatus that displays the surgical site image.

<18>

A program that cause a computer to function as a control unit configured to control to perform correction processing on a surgical site image as a captured surgical site on the basis of information related to display of a display apparatus that displays the surgical site image.

<19>

A surgical system including:

an endoscope configured to photograph an image;

a control unit configured to control to perform correction processing on a surgical site image as a captured surgical site photographed by the endoscope, on the basis of information related to display of a display apparatus that displays the surgical site image; and the display apparatus configured to display a corrected surgical site image that has undergone the correction processing.

<20>

The surgical system according to <19>, in which the control unit controls to perform the correction processing on the basis of the information related to the display of each of a plurality of display apparatuses in a case where the surgical site image is to be displayed on the plurality of display apparatuses.

<O1>

An image processing apparatus including an image processing unit configured to perform image processing on a surgical site image as a captured surgical site, the image processing having an intensity corresponding to a monitor size of a monitor that displays the surgical site image.

<O2>

The image processing apparatus according to <O1>, in which the image processing unit performs one or both of noise removal processing and enhancement processing, as the image processing.

<O3>

The image processing apparatus according to <O2>, in which the image processing unit performs noise removal processing such that the larger the monitor size, the higher the intensity of noise removal processing, and performs enhancement processing such that the smaller the monitor size, the higher the intensity of enhancement processing.

<O4>

The image processing apparatus according to any of <O1> to <O3>, further including a monitor size acquisition unit that obtains the monitor size.

<O5>

The image processing apparatus according to <O4>, in which the monitor size acquisition unit obtains the monitor size to be input by user operation on a user interface (UI).

<O6>

The image processing apparatus according to <O4>, in which the monitor size acquisition unit obtains the monitor size transmitted from the monitor.

<O7>

The image processing apparatus according to any of <O1> to <O3>, further including a monitor size estimation unit that estimate the monitor size from a monitor photographed image obtained by photographing the monitor.

<O8>

The image processing apparatus according to <O7>, in which the monitor size estimation unit estimates the monitor size on the basis of the number of pixels on which the monitor is captured among the pixels of the monitor photographed image.

<O9>

The image processing apparatus according to <O7>, in which the monitor size estimation unit estimates the monitor size on the basis of the number of pixels on which the monitor is captured among the pixels of the monitor photographed image and a photographing distance when the monitor is photographed.

<O10>

The image processing apparatus according to <O9>, in which the monitor photographed image is an image of at least two viewpoints photographed by a multi-view camera, and the monitor size estimation unit estimates the photographing distance from the image of the two viewpoints.

<O11>

The image processing apparatus according to <O9>, in which the monitor photographed image is an image of two viewpoints photographed at different timings from different photographing positions, and the monitor size estimation unit estimates the photographing distance from the image of the two viewpoints.

<O12>

The image processing apparatus according to any of <O1> to <O11>, in which the image processing unit performs image processing with an intensity corresponding to each of a plurality of monitor sizes and outputs the surgical site image that has undergone image processing for each of the plurality of monitor sizes.

<O13>

The image processing apparatus according to any of <O1> to <O12>, in which the image processing unit performs the image processing using parameters determined in accordance with the monitor size, so as to perform image processing with an intensity corresponding to the monitor size.

<O14>

The image processing apparatus according to any of <O1> to <O12>, in which the image processing unit performs the image processing with an image processing scheme determined in accordance with the monitor size, so as to perform image processing with an intensity corresponding to the monitor size.

<O15>

An image processing method including performing image processing on a surgical site image as a captured surgical site, the image processing having an intensity corresponding to a monitor size of a monitor that displays the surgical site image.

<O16>

A program that causes a computer to function as an image processing unit configured to perform image processing on a surgical site image as a captured surgical site, the image processing having an intensity corresponding to a monitor size of a monitor that displays the surgical site image.

<O17>

A surgical system including:

an endoscope configured to photograph an image;

an image processing unit configured to perform image processing on a surgical site image as a captured surgical site photographed by the endoscope, the image processing having an intensity corresponding to a monitor size of a monitor that displays the surgical site image; and the monitor configured to display the surgical site image that has undergone the image processing by the image processing unit.

<O18>

The surgical system according to <O17>, further including a monitor size estimation unit that estimates the monitor size from a monitor photographed image obtained by photographing the monitor by the endoscope.

<O19>

The surgical system according to <O18>, in which the endoscope photographs an image with a multi-view camera, and the monitor size estimation unit estimates a photographing distance when the monitor is photographed from among monitor photographed images of two viewpoints photographed by the multi-view camera, and estimates the monitor size on the basis of the number of pixels on which the monitor is captured among the pixels in the monitor photographed image and the photographing distance when the monitor is photographed.

<O20>

The surgical system according to any of <O17> to <O19>, further including a camera control unit (CCU) configured to control a camera head of the endoscope, in which the image processing unit is provided in any of the CCU and the monitor, or both of the CCU and the monitor.

REFERENCE SIGNS LIST

11 Patient bed
12 Patient
12A Affected portion
13 to 16 Trocar
21 Endoscope
22 Pneumoperitoneum needle
23 Energy treatment tool
24 Forceps
30 Cart
31 CCU
31A Camera cable
32 Light source apparatus
32A Light guide cable
33 Treatment tool apparatus
34 Pneumoperitoneum apparatus
35 Recorder
36 Printer
37, 37A Monitor
38 Foot switch
41 UI
42 Image processing parameter determination unit
43 Image processing unit
51 Monitor size acquisition unit
52 Parameter storage unit
53 Determination unit
61 Monitor size estimation unit
71 Monitor frame detector
72 Monitor size converter
81 UI
82 Monitor size converter
91 Depth estimation unit
92 Monitor photographing distance estimation unit
101 Depth estimation unit
111 Image display unit
121 Image processing scheme determination unit
122 Image processing unit
131 Monitor size acquisition unit
132 Image processing scheme storage unit
133 Determination unit
201 Bus 202 CPU
203 ROM
204 RAM
205 Hard disk
206 Output unit
207 Input unit
208 Communication unit
209 Drive
210 Input/output interface
211 Removable recording medium

The invention claimed is:

1. An image processing apparatus comprising:
processing circuitry configured to
receive a surgical site image corresponding to a captured surgical site,
receive information related to a display that displays the surgical site image, wherein the information related to the display includes a display screen size, wherein the processing circuitry for determining the display screen size is further configured to
receive a photograph of the display, wherein the photograph is captured at a predetermined distance from the display,
detect a frame of the display by performing edge detection on the display in the photograph, and
determine the display screen size based on the detected frame of the display, and
perform correction processing on the surgical site image based on the display screen size.

2. The image processing apparatus according to claim 1, wherein the information related to the display further includes display resolution and brightness of the display apparatus.

3. The image processing apparatus according to claim 1, wherein the processing circuitry is further configured to perform correction processing on the surgical site image based on the information related to the display and usage conditions of the display apparatus.

4. The image processing apparatus according to claim 3, wherein the usage conditions include brightness of a display apparatus installation location, a viewing distance and a viewing time of a viewer of the display apparatus.

5. The image processing apparatus according to claim 1, wherein the processing circuitry is further configured to control the intensity of the correction processing based on the information related to the display.

6. The image processing apparatus according to claim 1, wherein the correction processing includes noise removal processing, edge enhancement processing, contrast adjustment processing, and parallax adjustment processing.

7. The image processing apparatus according to claim 1, wherein the processing circuitry is further configured to control a processing scheme of the correction processing based on the information related to the display.

8. The image processing apparatus according to claim 1, further including a storage unit that stores correction processing appropriate for the display in association with the information related to the display,
wherein the processing circuitry is further configured to perform the correction processing on the surgical site image based on the correction processing stored in the storage unit.

9. The image processing apparatus according to claim 1, wherein the processing circuitry is further configured to obtain the information related to the display.

10. The image processing apparatus according to claim 9, wherein the processing circuitry is further configured to obtain the information related to the display from the display apparatus.

11. The image processing apparatus according to claim 1, wherein the photograph of the display is an image of at least two viewpoints photographed by a multi-view camera, and
the processing circuitry is further configured to estimate a photographing distance from the image of the two viewpoints.

12. The image processing apparatus according to claim 1, wherein the processing circuitry is further configured to estimate the photographing distance from focus information of the photographed image.

13. The image processing apparatus according to claim 1, wherein the processing circuitry is further configured to perform the correction processing based on the information related to the display of each of a plurality of display apparatuses in a case where the surgical site image is to be displayed on the plurality of display apparatuses.

14. The image processing apparatus according to claim 1, wherein the processing circuitry is further configured to display a corrected surgical site image that has undergone the correction processing, on the display.

15. An image processing method comprising:
receiving a surgical site image corresponding to a captured surgical site;
receiving information related to a display that displays the surgical site image, wherein the information related to the display includes a display screen size, wherein determining the display screen size includes
receiving a photograph of the display, wherein the photograph is captured at a predetermined distance from the display,
detecting a frame of the display by performing edge detection on the display in the photograph, and
determining the display screen size based on the detected frame of the display; and
performing correction processing on the surgical site image based on the display screen size.

16. A non-transitory computer-readable storage medium storing computer-readable instructions thereon which, when executed by a computer, cause the computer to perform a method, the method comprising:
receiving a surgical site image corresponding to a captured surgical site;
receiving information related to a display that displays the surgical site image, wherein the information related to the display includes a display screen size, wherein determining the display screen size includes
receiving a photograph of the display, wherein the photograph is captured at a predetermined distance from the display,
detecting a frame of the display by performing edge detection on the display in the photograph, and
determining the display screen size based on the detected frame of the display; and
performing correction processing on a surgical site image as a captured surgical site based on the display screen size.

17. A surgical system comprising:
an endoscope configured to photograph one or more images;
processing circuitry configured to
- receive a surgical site image from the endoscope corresponding to a captured surgical site,
- receive information related to a display that displays the surgical site image, wherein the information related to the display includes a display screen size, wherein the processing circuitry for determining the display screen size is further configured to
  - receive a photograph of the display from the endoscope, wherein the photograph is captured at a predetermined distance from the display,
  - detect a frame of the display by performing edge detection on the display in the photograph, and
  - determine the display screen size based on the detected frame of the display, and
- perform correction processing on the surgical site image based on the display screen size; and
a display apparatus including the display, the display apparatus being configured to display a corrected surgical site image that has undergone the correction processing.

18. The surgical system according to claim 17, wherein the processing circuitry is further configured to perform the correction processing based on the information related to the display of each of a plurality of display apparatuses in a case where the surgical site image is to be displayed on the plurality of display apparatuses.

* * * * *